(12) United States Patent
Bau et al.

(10) Patent No.: US 8,702,927 B2
(45) Date of Patent: Apr. 22, 2014

(54) MULTIPLE-ELECTRODE AND METAL-COATED PROBES

(75) Inventors: Haim H. Bau, Swarthmore, PA (US); Michael G. Schrlau, Drexel Hill, PA (US); Rui Zhang, Bismarck, ND (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 52 days.

(21) Appl. No.: 13/263,234

(22) PCT Filed: Apr. 23, 2010

(86) PCT No.: PCT/US2010/032191
§ 371 (c)(1),
(2), (4) Date: May 24, 2012

(87) PCT Pub. No.: WO2010/124177
PCT Pub. Date: Oct. 28, 2010

(65) Prior Publication Data
US 2012/0282644 A1 Nov. 8, 2012

Related U.S. Application Data

(60) Provisional application No. 61/172,321, filed on Apr. 24, 2009.

(51) Int. Cl.
*G01N 27/26* (2006.01)
*C12M 1/42* (2006.01)
*C12M 1/34* (2006.01)

(52) U.S. Cl.
USPC .................. 204/403.01; 422/68.1; 422/82.01; 435/287.1; 435/29; 435/306.1; 600/547; 324/724

(58) Field of Classification Search
USPC ......... 204/400, 403.01; 435/287.1, 287.2, 29, 435/306.1; 422/68.1, 425, 82.01; 600/309–367, 547; 324/724
See application file for complete search history.

(56) References Cited

U.S. PATENT DOCUMENTS

| | | | |
|---|---|---|---|
| 4,153,418 A | 5/1979 | Haas | |
| 4,640,821 A | 2/1987 | Mody et al. | |
| 4,799,484 A * | 1/1989 | Smith et al. | 606/223 |
| 5,350,419 A * | 9/1994 | Bendel et al. | 607/132 |
| 5,514,425 A | 5/1996 | Ito et al. | |
| 6,063,629 A | 5/2000 | Knoblauch | |
| 6,135,990 A * | 10/2000 | Heller et al. | 604/500 |
| 7,824,620 B2 | 11/2010 | Bau et al. | |
| 7,964,159 B2 | 6/2011 | Bau et al. | |
| 2004/0138622 A1 | 7/2004 | Palasis | |
| 2004/0182707 A1 * | 9/2004 | Jardemark et al. | 204/451 |
| 2004/0241681 A1 | 12/2004 | Korchev et al. | |
| 2006/0115971 A1 * | 6/2006 | Bau et al. | 438/591 |

FOREIGN PATENT DOCUMENTS

WO WO 2008/130463 10/2008

OTHER PUBLICATIONS

Sigma-Aldrich Needle Gauge Chart, downloaded Apr. 9, 2013.*
Schrlau et al., "Carbon-Based Nanoprobes for Cell Biology", Microfluid Nanofluid, May 2009, 7, 439-450.

* cited by examiner

*Primary Examiner* — Jennifer Dieterle
(74) *Attorney, Agent, or Firm* — Woodcock Washburn, LLP

(57) ABSTRACT

Provided are probes featuring multiple electrodes, which probes have diameters in the nanometer range and may be inserted into cells or other subjects so as to monitor an electrical characteristic of the subject. The probes may also include a conductive coating on at least one probe element to improve the probes' performance. The probes may also be used to inject a fluid or other agent into the subject and simultaneously monitor changes in the subject's electrical characteristics in response to the injection. Related methods of fabricating and of using the inventive probes are also provided.

26 Claims, 43 Drawing Sheets

Figure 25
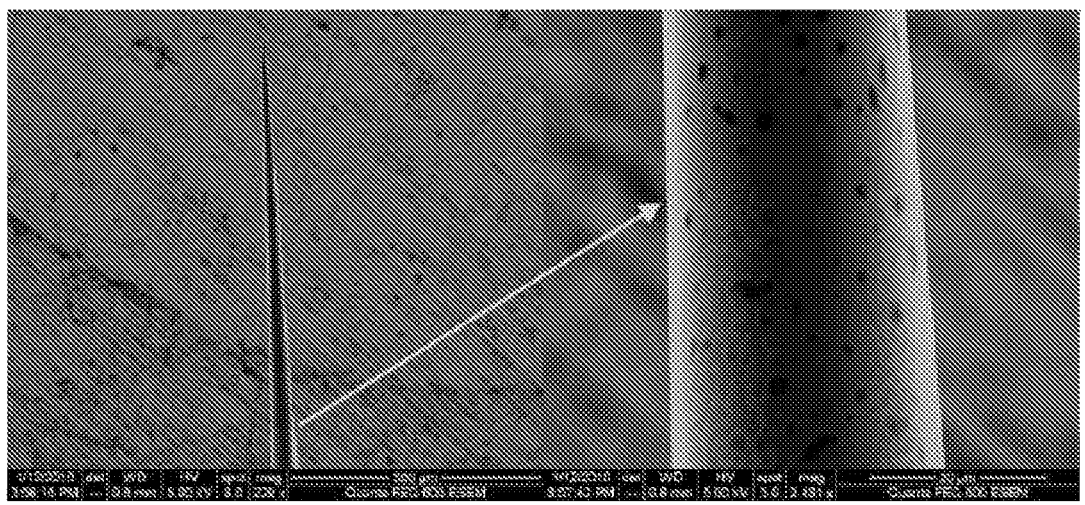
(a)
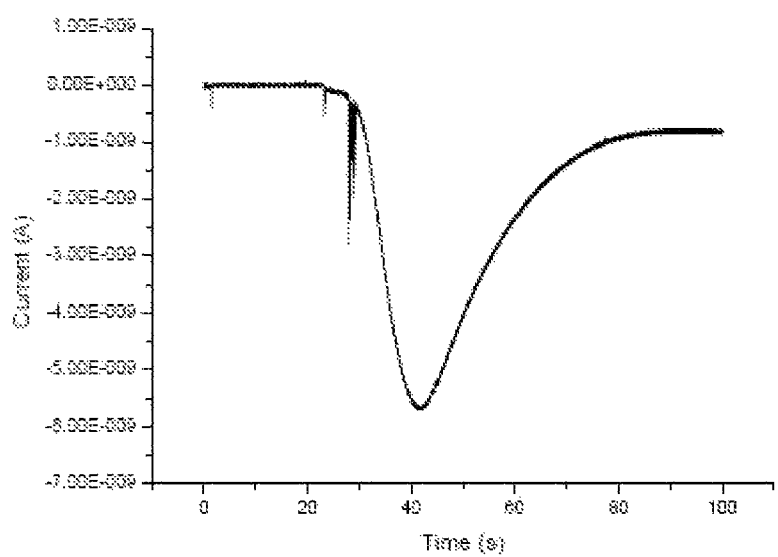
(b)

Figure 26
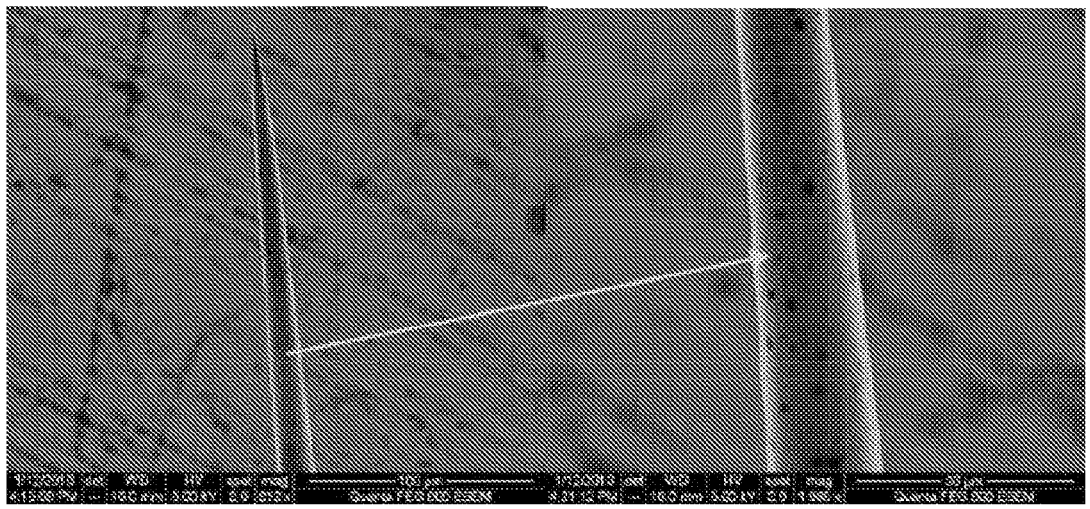
(a)
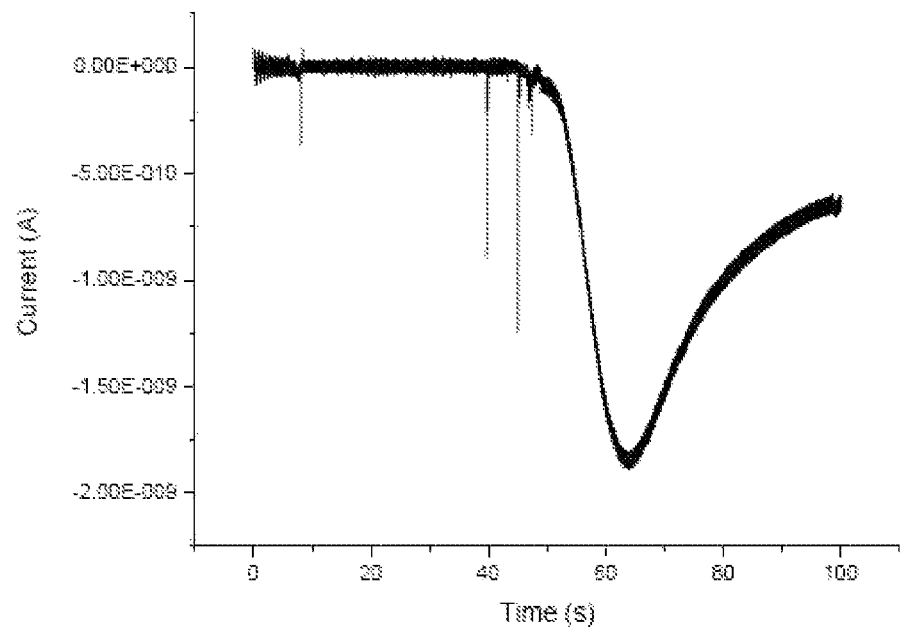
(b)

Figure 27
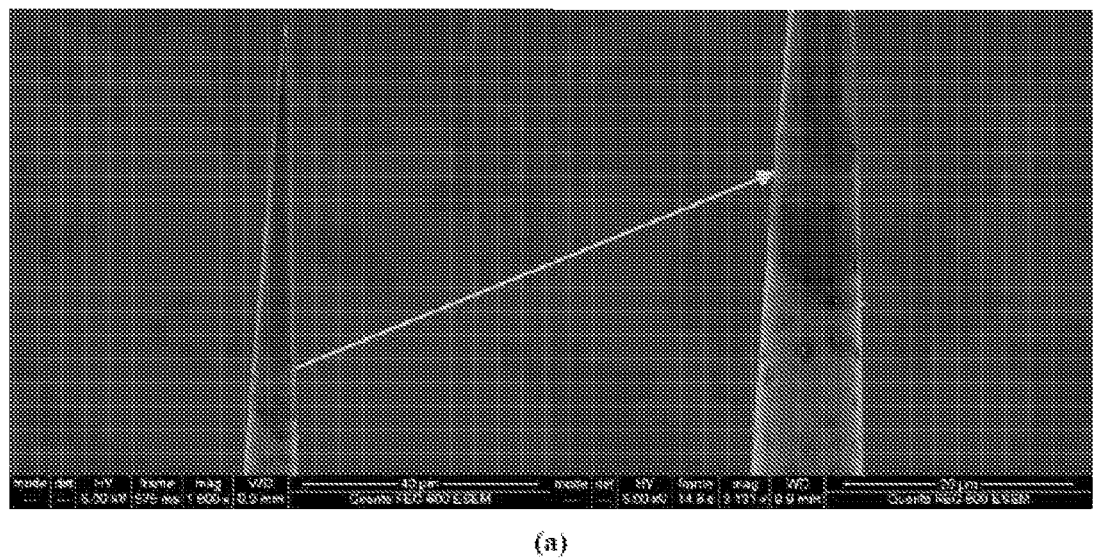
(a)
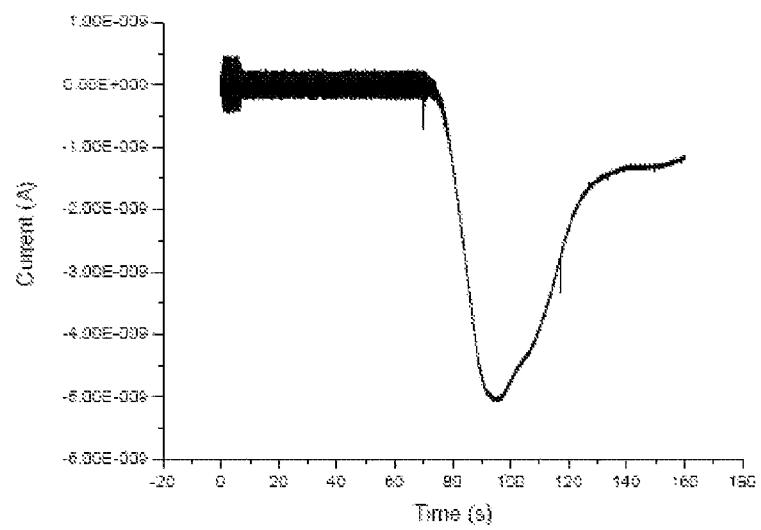
(b)

Figure 28
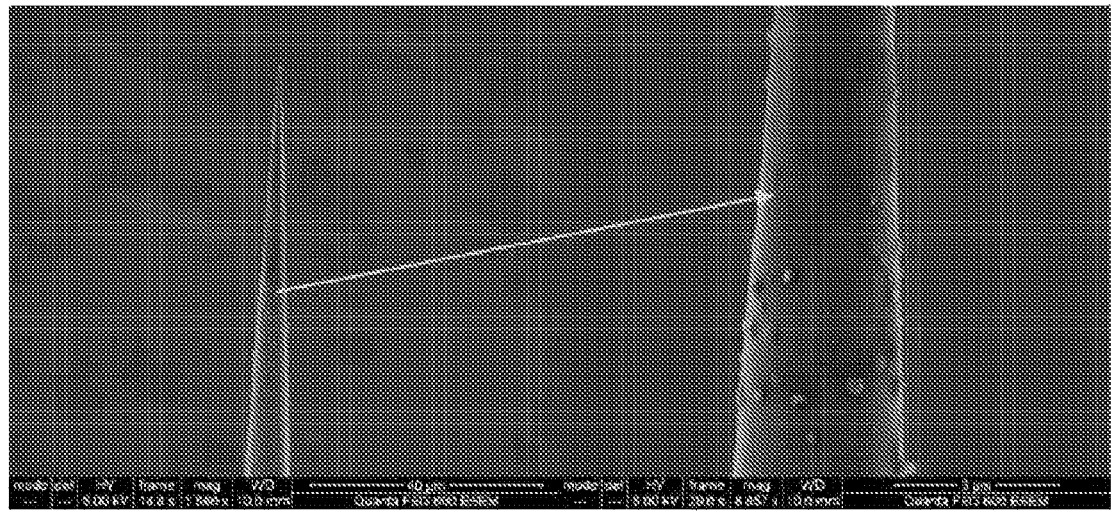
(a)
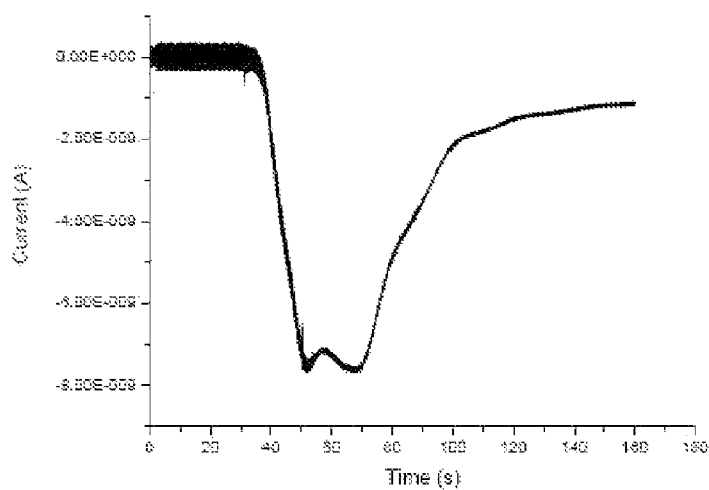
(b)

Figure 29
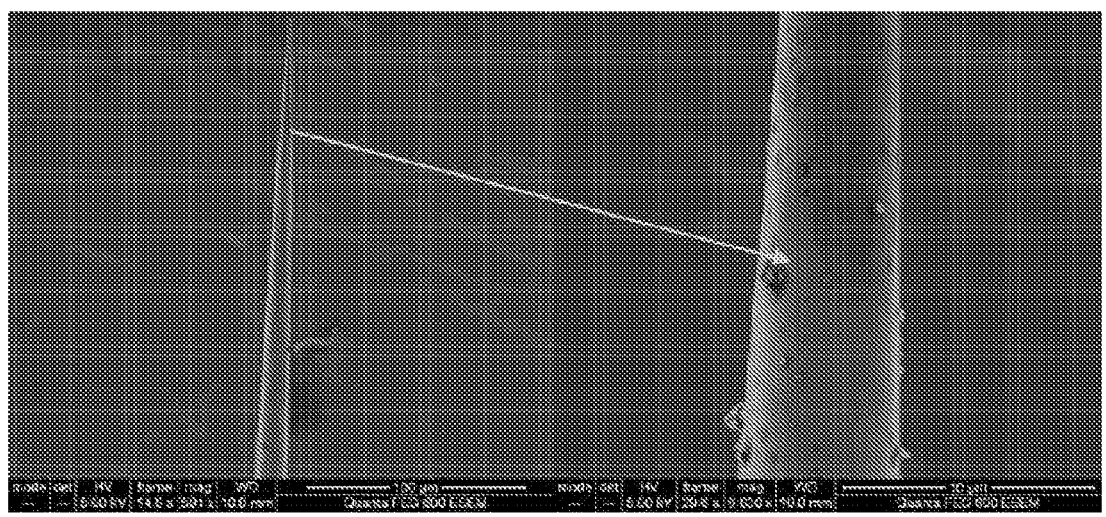
(a)
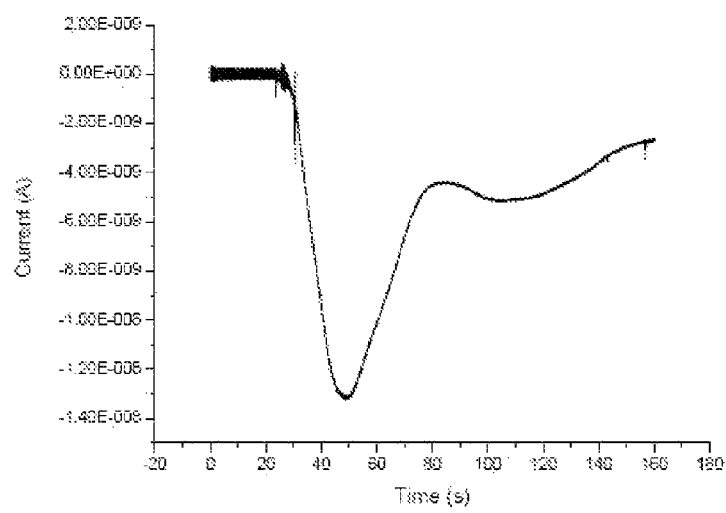
(b)

Figure 30
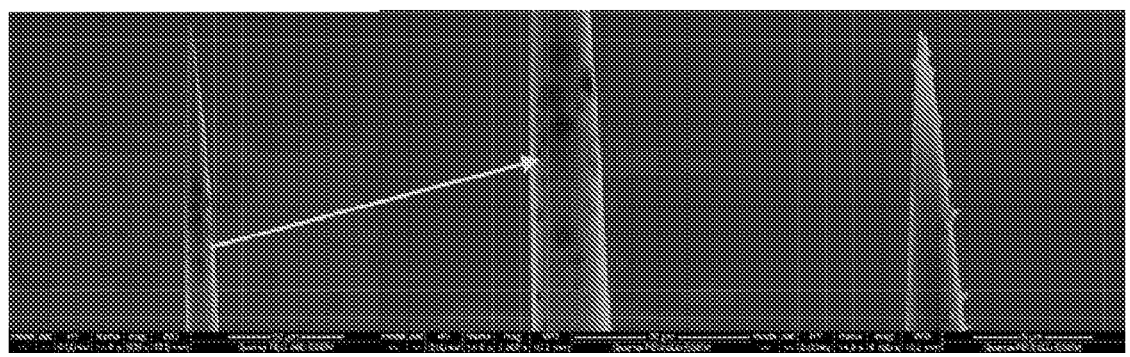
(a)
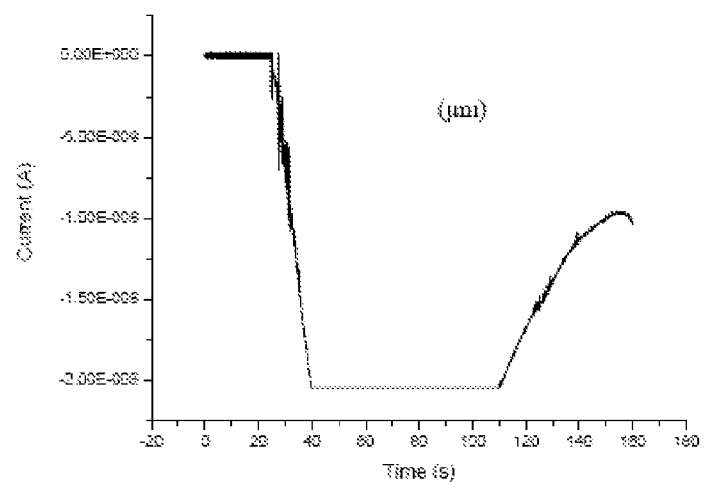
(b)

Figure 31
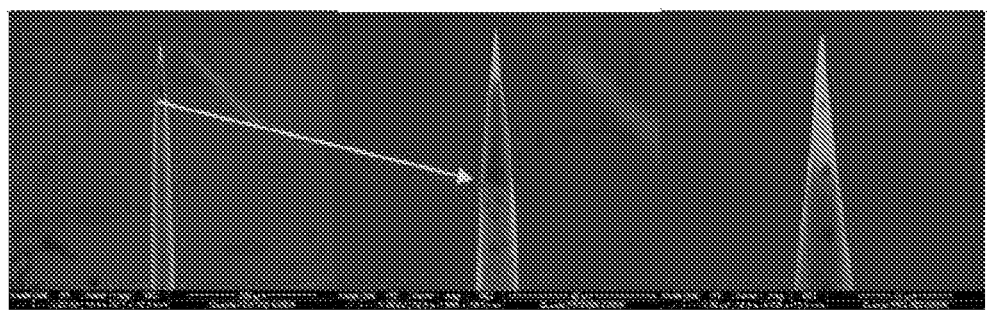
(a)
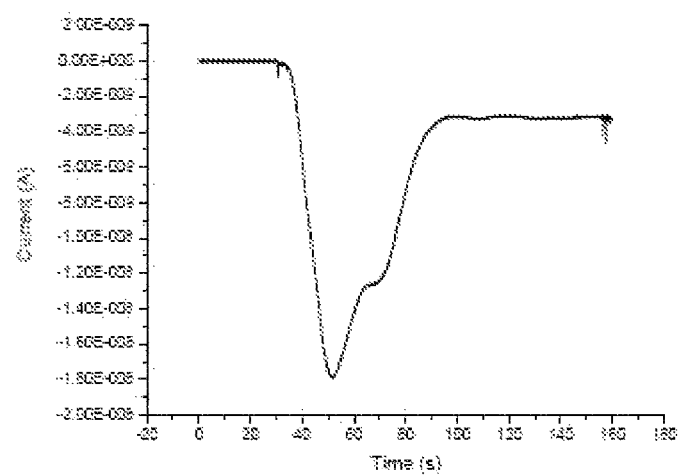
(b)

Figure 32
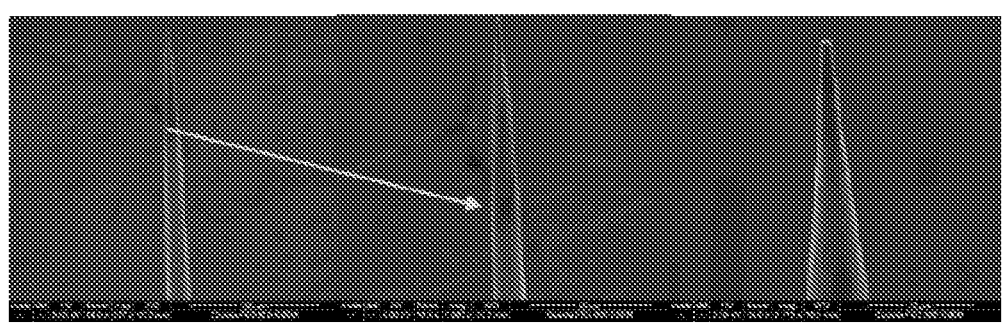
(a)
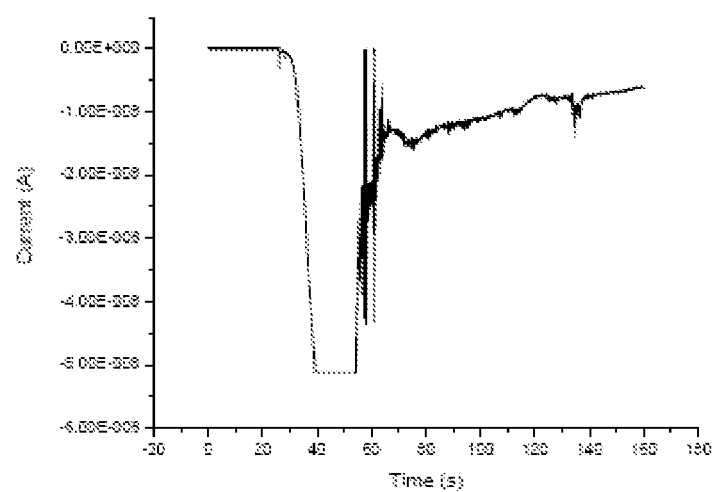
(b)

Figure 33
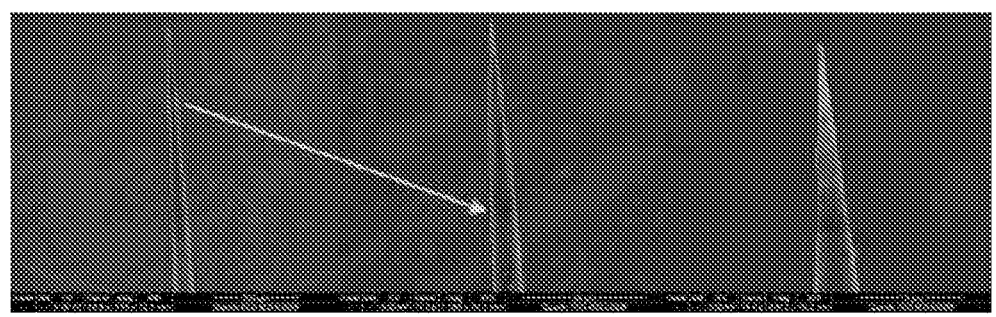
(a)
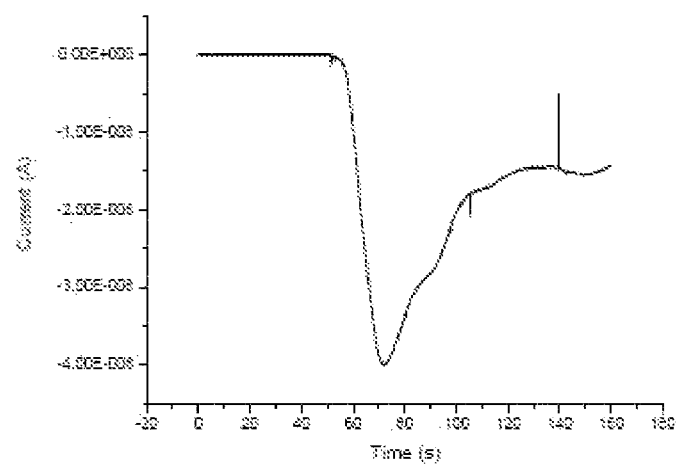
(b)

MULTIPLE-ELECTRODE AND METAL-COATED PROBES

CROSS-REFERENCE TO RELATED APPLICATIONS

This application is the National Stage of International Application No. PCT/US2010/032191, filed Apr. 23, 2010, which claims the benefit of U.S. Provisional Application No. 61/172,321, filed Apr. 24, 2009, the disclosures of which are incorporated herein by reference in their entireties for all purposes.

TECHNICAL FIELD

The present invention relates to the field of nanopipettes and to the field of electrodes.

BACKGROUND

Cellular probes designed to monitor electrophysiological events play an important role in experimental cell biology and pharmacology. In modern electrophysiology, electrolyte-filled glass micropipettes are utilized to access intracellular domains in order to measure how a stimulus affects the flow of ions through or changes the electrical potential across the cell membrane. Traditionally, electrical measurements in small cells are measured with either large-tipped, glass micropipettes filled with intracellular solution or fine-tipped, glass micropipettes filled with highly concentrated salt solution.

While versatile and widely-used, the patch-clamp technique ruptures the cell membrane and alters the internal milieu of a cell, preventing both long-term and repetitive monitoring. In contrast, fine-tipped, glass microelectrodes are less intrusive and therefore are more likely to spare a cell from irreparable damage. However, cell damage may still occur during prolonged measurement when the high-concentration electrolyte contained in the pipette's lumen diffuses into the cell. Problems that impact intracellular recording techniques and degrade recording performance include clogging of the electrode tip, collecting debris at the tip during probe penetration, and tip damage upon approaching and penetrating the cell.

To address some of these shortcomings, ohmic nanoelectrodes for intracellular recording have been proposed by others. Ohmic nanoelectrodes penetrate through tissue and into cells, measure electrical signals without altering cell characteristics. These devices, however, are not capable of both intracellular delivery and electrical recording. Thus, there is a need in the art for devices and methods for monitoring intracellular conditions while also having the ability to deliver agents to the intracellular region.

SUMMARY

In addressing the described challenges, the present invention first provides probes comprising an elongate insulator having a distal terminus and a lumen, the lumen having a diameter of from about 1 nm to about 1 cm; a first conductive layer on the inner surface of the lumen and in electrical communication with a first contact; and a second conductive layer surmounting at least a portion of the outer surface of the elongate insulator and in electrical contact with a second contact.

Also disclosed are methods of fabricating probes. These methods suitably include disposing a first conductive layer along at least a portion of the inner surface of an elongate insulator having a lumen; disposing a second conductive layer along at least a portion of the outer surface of the elongate insulator; removing a portion of the second conductive layer such that the second conductive layer terminates at a position remote from the terminus of the elongate insulator, or removing a portion of the first conductive layer such that the first conductive layer terminates at a position remote from the distal terminus of the elongate insulator.

Additionally provided are methods of analysis. These methods include inserting a portion of a probe through an outer boundary of a subject, the probe comprising (a) an elongate insulator having a lumen, (b) a first conductive layer on the inner surface of the lumen and in electrical communication with a first contact, (c) a second conductive layer surmounting at least a portion of the outer surface of the elongate insulator and in electrical contact with a second contact, the inserting being performed such that either the first conductive material or the second conductive material resides within the subject; monitoring a first electrical signal from within the subject, and comparing the electrical signal from within the cell to a second electrical signal measured from a reference material exterior to the subject.

Also disclosed are probes. These probes suitably include an elongate insulator having a lumen, said lumen having a diameter of from about 1 nm to about 1 cm; a first conductive layer on the inner surface of the lumen and in electrical communication with a first contact; a second conductive layer surmounting at least a portion of the outer surface of the elongate insulator and in electrical contact with a second contact; and the first conductive layer and the second conductive layer disposed such that a portion of the first hollow insulator is surmounted by either the first electronically conductive layer or the second electronically conductive layer.

Further provided are probes. These probes suitably include an elongate insulator having a lumen and a distal terminus, said lumen having a diameter of from about 1 nm to about 1 cm; a first conductive layer on the inner surface of the lumen and in electrical communication with a first contact; a second conductive layer surmounting at least a portion of the outer surface of the elongate insulator and in electrical contact with a second contact; and the first conductive layer and the second conductive layer disposed such that a portion of the first conductive layer or the second conductive layer extends beyond the distal end of the elongate insulator.

The present invention also provides methods of fabricating a probe. The methods include disposing a first conductive layer along at least a portion of the inner surface of an elongate insulator having a lumen; disposing a second conductive layer along at least a portion of the outer surface of the elongate insulator; removing at least a portion of the elongate insulator, at least a portion of the first conductive layer, at least a portion of the second conductive layer, or any combination thereof, such that a portion of the elongate insulator is surmounted by either the first conductive layer or by the second conductive layer.

Also disclosed are methods of assessing the condition of a probe. These assessment methods include measuring the impedance between (A) an electrode disposed within a probe comprising (i) an elongate insulator having a lumen, said lumen having a diameter of from about 1 nm to about 1 cm, (ii) a first conductive layer on the inner surface of the lumen and in electrical communication with a first contact, (iii) a second conductive layer surmounting at least a portion of the outer surface of the elongate insulator and in electrical contact with a second contact, and (B) an electrode contacting a reference material exterior to the probe; and comparing the impedance to a reference value.

Also provided are probes, comprising a hollow insulating handle comprising a first material, the handle comprising an exterior cross-sectional dimension of 500 microns at a point along the handle's length, the handle tapering to a distal end, the distal end of the handle comprising an interior cross-sectional dimension in the range of from about 10 nm to about 100 microns; and a capillary probe or fiber probe of a second material, said capillary or fiber probe conforming to at least a portion of the inner surface of the hollow macroscopic handle at the distal end, the second material comprising a carbonaceous material, a metal, a semiconductor, or any combination thereof, and a portion of the second material extending beyond the handle, said portion of the second material extending beyond the handle being at least partially surmounted by a metal coating.

Further provided are methods of fabricating a probe, comprising exposing a portion of a conductive material beyond the terminus of an elongate insulator within which insulator the conductive material is disposed; electroplating at least a portion of the exposed portion of conductive material with a metal.

BRIEF DESCRIPTION OF THE DRAWINGS

FIG. 25 illustrates (a) SEM images of CNP with 40 nm Ti layers etched in oil covered HF. A 510 µm length of titanium was etched. (b) The current as a function of the etching time;

FIG. 26 illustrates (a) SEM images of CNP with 40 nm Ti layers etched in oil covered HF. A 150 µm length of titanium was etched. (b) The current as a function of the etching time;

FIG. 27 illustrates (a) SEM images of CNP with 100 nm Ti layer etched in oil covered BHF. A length of 72 µm of titanium was etched. (b) The current as a function of the etching time;

FIG. 28 illustrates (a) SEM images of CNP with 100 nm Ti layers etched in oil covered HF. A length of 43 µm of titanium was etched. (b) The current as a function of the etching time;

FIG. 29 illustrates (a) SEM images of CNP with 100 nm Ti layers etched in oil covered BHF. A length of 55 µm of titanium was etched. (b) The current as a function of the etching time;

FIG. 30 illustrates (a) SEM images of CNP with ~15 carbon tip and 100 nm Ti layers etched in oil covered HF. 98 µm Ti tip was etched. ~7.5 µm carbon tip left after Ti etching (b) Relationship between current and etching time;

FIG. 31 illustrates (a) SEM images of CNP with ~15 µm carbon tip 100 nm Ti layers etched in oil covered HF. 42 µm Ti tip was etched. ~14 µm carbon tip left after Ti etching (b) Relationship between current and etching time;

FIG. 32 illustrates (a) SEM images of CNP with ~15 µm carbon tip 100 nm Ti layers etched in oil covered HF. 88 µm Ti tip was etched. ~10 µm carbon tip left after Ti etching (b) Relationship between current and etching time;

FIG. 33 illustrates (a) SEM images of CNP with ~15 µm carbon tip 100 nm Ti layers etched in oil covered HF. 90 µm Ti tip was etched. ~11 µm carbon tip left after Ti etching (b) Relationship between current and etching time;

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first embodiment, the present invention provides probes, comprising an elongate insulator having a lumen. The lumen suitably has a diameter of from about 1 nm to about 1 cm, with a first conductive layer on the inner surface of the lumen and in electrical communication with a first contact. The probes include a second conductive layer surmounting at least a portion of the outer surface of the elongate insulator and in electrical contact with a second contact.

The lumens of the present invention are preferably circular in cross-section, although lumens of different cross-sectional shape are suitable, and can even be polygonal or slit-shaped in cross-section. The cross-section may be constant along the length of the insulator, or may vary. In one especially suitable embodiment, the lumen of the insulator tapers.

The diameter of a lumen is suitably defined as the widest distance across the void space of the lumen, measured perpendicular to the long axis of the lumen. The "outer surface" of the insulator is defined as the exterior surface of the insulator. "Elongate" refers to a form that has its longest dimension perpendicular to the lumen, such as a tube. "Conductive" refers to the characteristic of being electronically conductive.

Figure 3:
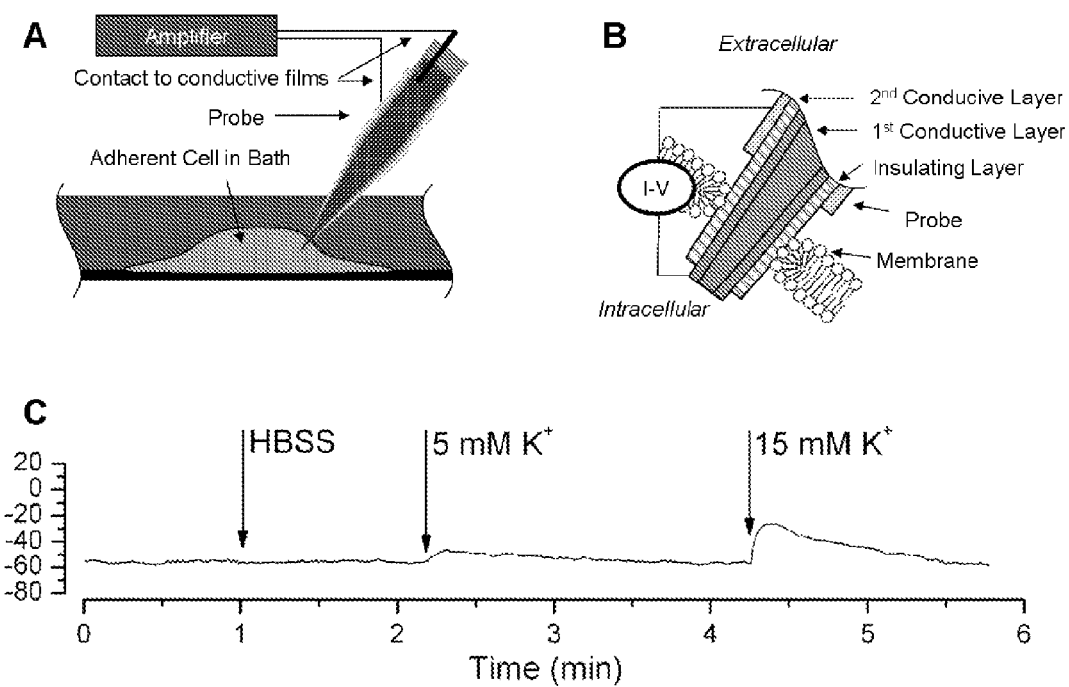
FIG. 3 illustrates detecting electrical signals with multielectrode probes. (A) Overall strategy for using the probe in cell experiments. (B) A close-up of how the probe penetrates the cell membrane and measures across the membrane with the intracellular and extracellular electrodes. (C) Actual voltage recording showing cell depolarization upon increases in extracellular potassium ion concentration.

In some embodiments, the second conductive layer terminates at a position remote from the distal terminus of the elongate insulator. Preferably, the distance between the terminus of the second conductive layer and the distal end of insulator is greater than the thickness of the cell wall or other barrier across which the probe may be inserted, as shown in, e.g., FIG. 3.

Elongate insulators suitable for the claimed invention suitably includes dielectric materials such as silica, silica nitride, glass, quartz, polymer, plastic, and the like. Pulled glass pipettes—such as described in U.S. application Ser. No. 11/231,425—are especially suitable. The insulator is suitably a solid, but flexible materials may also be used.

The lumen of the elongate insulator suitably has a diameter in the range of from about 10 nm to about 10,000 nm, or from about 50 to about 1000 nm, or from 100 to about 500 nm. In some embodiments, the insulators have inner diameters of as small as about 5 microns, 2 microns, 1 micron (1000 nm), 500 nm, 300 nm and even as small as 100 nm.

The wall thickness of the elongate insulator in the range of from about 1 nm to about 10 micrometers, or from about 50 nm to about 5 microns, or even from about 100 nm to about 1 micron. Various materials are suitable for the first conductive layer and the second conductive layer, or both. Such materials include carbon, metal, a conductive polymer, and the like. Suitable metals include gold, silver, chromium, titanium, tungsten, platinum, aluminum, nickel, or any combination thereof.

The first conductive layer can have a thickness of from about 1 nm to about 10 micrometers, or from about 50 nm to about 1 micrometer, or from about 100 nm to about 500 nm. In some embodiments the thin films have thicknesses in the range of from about 1 nm to about 1000 nm. The thin film thicknesses can also be in the range of from about 2 nm to about 500 nm, from about 5 nm to about 250 nm, from about 10 nm to about 100 nm, from about 20 nm to about 50 nm, or any combination thereof. In some embodiments, the first conductive layer essentially fills the probe lumen such that the lumen is occluded (i.e., the inner diameter of the lumen is zero). In others, the first conductive layer defines a lumen, which lumen places the distal end of the probe in fluid communication with the opposing end of the probe.

The second conductive layer suitably has a thickness in the range of from about 1 nm to about 10 micrometers, or from about 50 nm to about 1 micrometer, or from about 100 nm to about 500 nm.

In some embodiments, the probe includes a second elongate insulator disposed adjacent to the second electronically conductive layer. The second elongate insulator suitably has a wall thickness in the range of from about 1 nm to about 10 micrometers, or from about 50 nm to about 5 microns, or even from about 100 nm to about 1 micron, although the first and second insulators need not be of the same thickness. The second elongate insulator suitably comprises dielectric materials such as silica, silica nitride, glass, quartz, polymer, plastic, and the like. The first and second insulators may be of the same or of different materials. The second elongate insulator is suitably coaxial with the first insulator.

Figure 1:
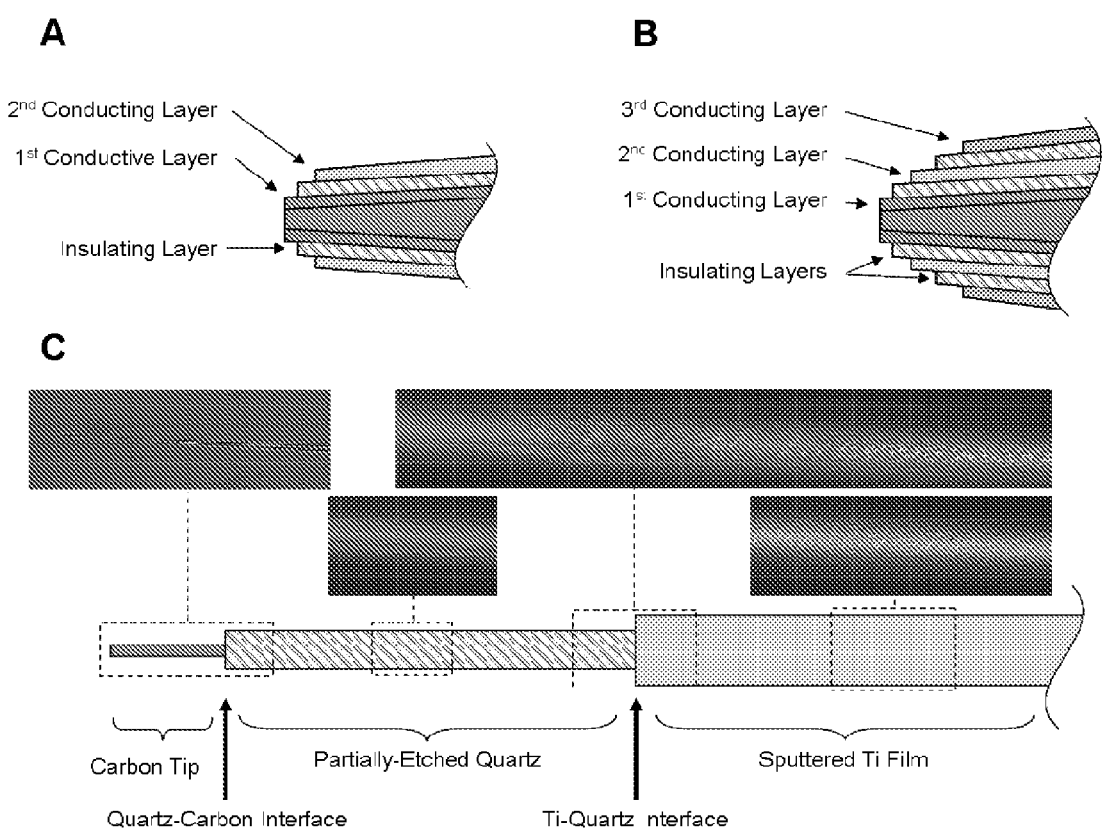
FIG. 1 illustrates a probe with multiple concentric electrodes. (A) A 2-electrode probe. (B) A 3-electrode probe. (C) An actual 2-electrode probe made with carbon and titanium electrodes separated by a quartz layer.

In some embodiments, the probe includes a third conductive layer surmounting at least at portion of the second elongate insulator, the third conductive layer in electrical communication with a third contact. The third conductive layer may be comprised of one or more of the conductive materials described elsewhere herein, and is suitably of a thickness of the first or second conductive layers. The first, second, and third conductive layers may all be of the same or of different thicknesses or of the same or different materials. One non-limiting embodiment of such probes is shown by FIG. 1, which figure illustrates a probe having first, second, and third conductive layers. As shown in that non-limiting figure, the various layers are tapered, coaxial cylinders.

Some probes further comprise a third elongate insulator disposed adjacent to the third conductive layer. The third insulator is suitably of the materials and wall thickness set forth in the description of the first and second insulators.

Probes may also include a fourth conductive layer surmounting at least a portion of the third elongate insulator, and the fourth conductive layer in electrical communication with a fourth contact. The fourth conductive layer is suitable of a material and wall thickness like those of the other conductive layers.

In some embodiments, the probe may include an injector in fluid communication with the lumen. The injector may be used to supply a volume of fluid through the lumen into, for example, a cell or other body into which the probe has been inserted.

In some embodiments, at least a portion of the first conductive layer extends beyond the distal terminus of the elongate insulator. This is shown in, e.g., FIG. 1(*c*), which figure shows (at the lower left) a carbon tip (i.e., the first conductive layer) extending beyond the end of the partially-etched quartz insulator.

Figure 41:
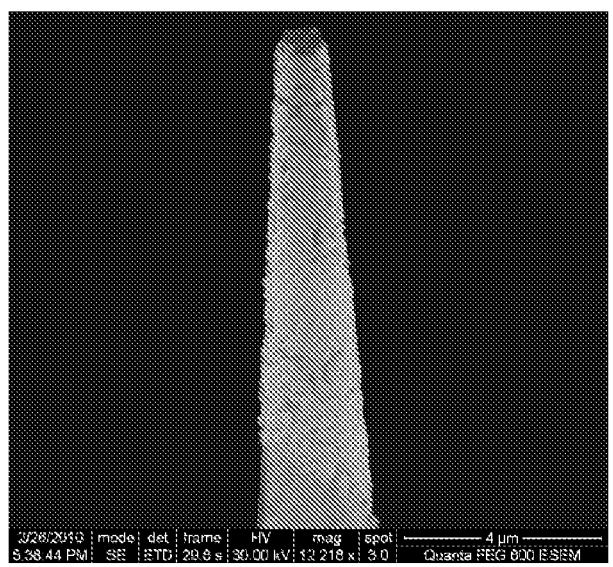
FIG. 41 illustrates a SEM image of the silver layer by double pulse potentiostatic deposition method.

As described herein, this extended portion (which may also be conceptualized as conductive material that is presented once a portion of the insulator is removed or etched away) may be surmounted at least in part by a metal. One such exemplary embodiment is shown in FIG. 41, which figure illustrates an SEM image of a silver layer disposed atop a carbonaceous probe tip, showing a smooth, continuous, and thin silver layer. While silver is shown in this illustrative embodiment, the invention should not be interpreted as being limited to silver, as other metals—such as gold and platinum—are also suitable for the inventive devices and methods.

The metal disposed atop the probe time suitably comprises a thickness in the range of from about 5 nm to about 1 micron, or from about 10 nm to about 500 nm, or even about 50 nm to about 100 nm. The user may obtain a metal film of the desired thickness by modulating process conditions.

Also provided are methods of fabricating probes. The methods include disposing a first conductive layer along at least a portion of the inner surface of an elongate insulator having a lumen; disposing a second conductive layer along at least a portion of the outer surface of the elongate insulator; removing a portion of the second conductive layer such that the second conductive layer terminates at a position remote from the distal terminus of the elongate insulator, or removing a portion of the first conductive layer such that the first conductive layer terminates at a position remove from the distal terminus of the elongate insulator.

Figure 2:
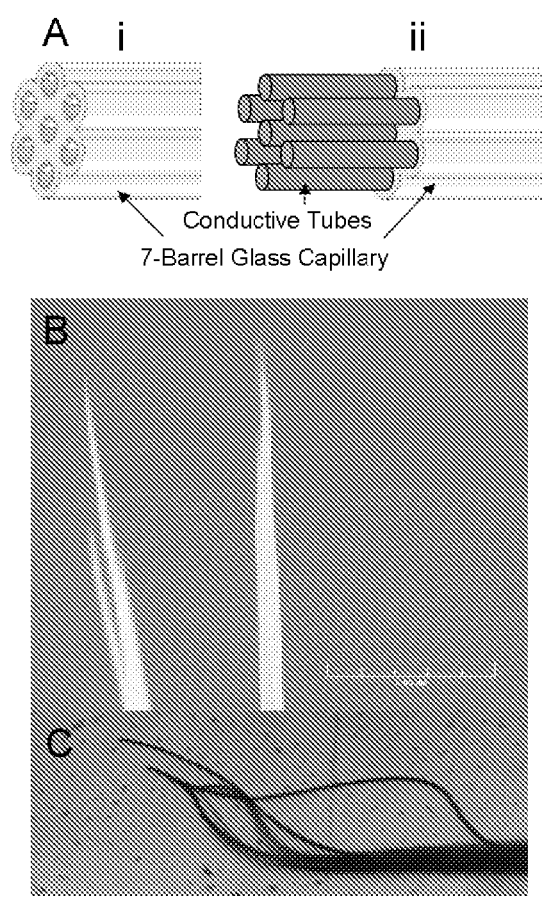
FIG. 2 illustrates probes with multiple electrode tips. (A) A multi-bore micropipette before (i) and after (ii) conductive layers were deposited. (B) SEM micrograph of carbon tips made from a 7-bore quartz micropipette. (C) Flexible characteristics of the carbon tips.

One non-limiting illustration of the claimed methods is shown in FIGS. 1 and 2. The methods may include removing a portion of the elongate insulator, as shown in FIG. 2.

Disposition of the first conductive layer is suitably accomplished by chemical vapor deposition, electroless plating, dessication, dipping, and the like. The first conductive layer may include carbon, metal, a conductive polymer, and the like—other suitable materials are described in additional detail elsewhere herein. Silver, gold, nickel, chromium, titanium, tungsten, and the like are all suitable metals.

Disposition of the second conductive layer may be accomplished by sputtering, electroless plating, dipping, spraying, chemical vapor deposition, dessicating, and the like. The second conductive layer may be carbon, a metal, and the like.

Removal of a conductive layer or the insulator may be accomplished by contact with an etchant, such as an acid. Buffered hydrofluoric acid is considered suitable. In some embodiments, the etchant preferentially removes the second conductive layer relative to the hollow insulator, or preferentially removes the second conductive layer relative to the first conductive layer. The etchant may also preferentially remove the first conductive layer relative to the insulator or the second conductive layer.

In some variants, the methods further include disposing an insulating material adjacent to the second conductive layer. This disposition may be accomplished by sputtering, evaporation, chemical vapor deposition, electroless deposition, spraying, dessication, dipping, or any combination thereof.

In some embodiments, a portion of the insulator is suitably removed such that a portion of the first conductive layer extends beyond the elongate insulator. This is illustrated by, e.g., FIGS. 1, 2, 11, and 36, which figures show insulator removal so as to expose or reveal a portion of the first conductive layer. As described elsewhere herein, the removal may be effected by an etchant, such as an acid. The etchant suitably preferentially etches the insulator over the first conductive layer.

The exposed conductive layer is suitably electroplated with a metal. This may be accomplished as described in the examples and other disclosure elsewhere herein. The additional of metal—particularly to a carbon electrode tip—improves the performance of the electronic probe and reduces the probe's noise level.

The invention also provides analysis methods. These methods include inserting a portion of a probe through an outer boundary of a subject, the probe comprising (a) an elongate insulator having a lumen, (b) a first conductive layer on the inner surface of the lumen and in electrical communication with a first contact, (c) a second conductive layer surmounting at least a portion of the outer surface of the elongate insulator and in electrical contact with a second contact, the inserting being performed such that either the first conductive material or the second conductive material resides within the subject; monitoring a first electrical signal from within the subject, and comparing the electrical signal from within the cell to a second electrical signal measured from a reference material exterior to the subject.

Cells, organelles, organs, tissues, and the like are all suitable subjects. The probe is suitably inserted into the subject such that a boundary of the subject—such as a cell membrane—forms an insulating seal against the probe, as shown in, e.g. FIGS. 3, 4, 5, and 6.

Figure 7:
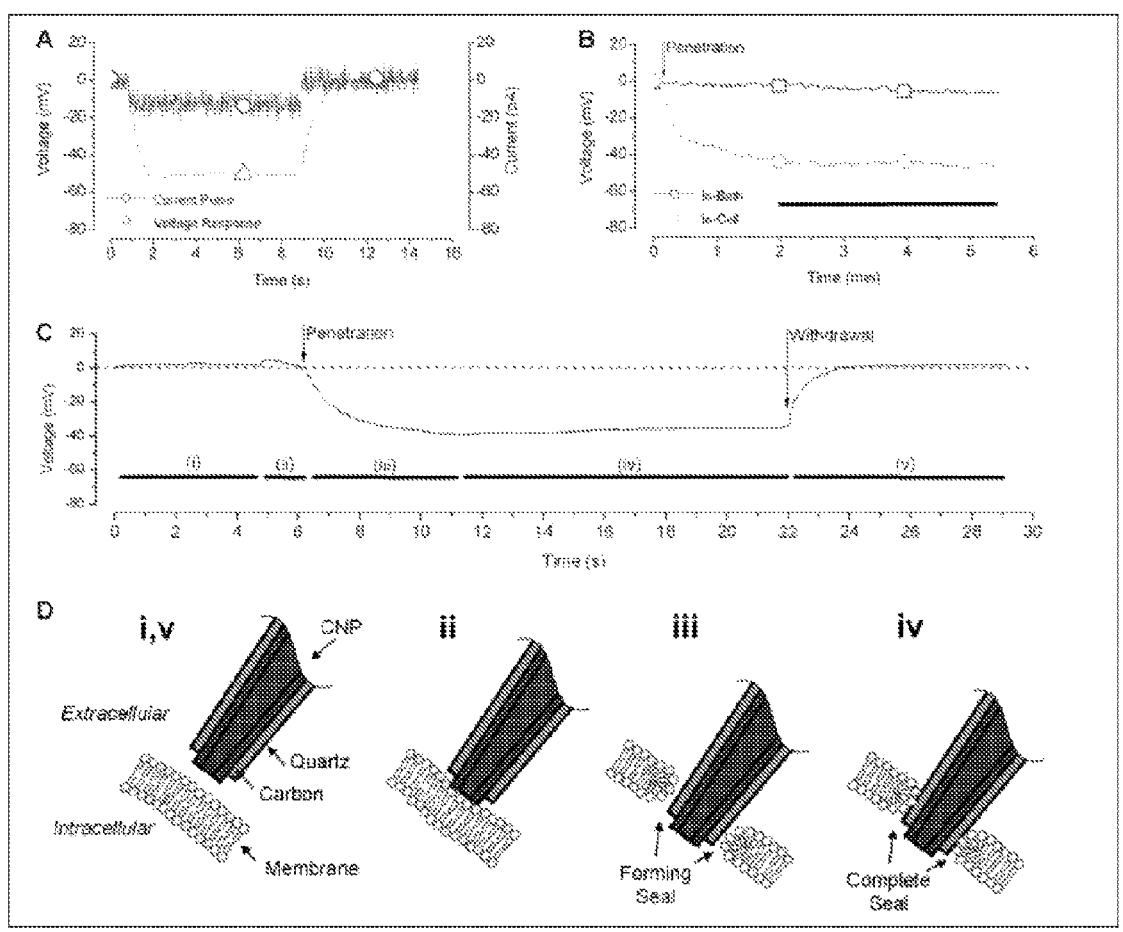
FIG. 7 illustrates measuring cell membrane potentials with CNPs. (A) Typical CNP voltage response (−50 mV) to a −10 pA current pulse measured vs. an Ag/Agcl reference electrode submerged in HBSS. (B) Voltage recording illustrating stable electrode performance (negligible drift over time, horizontal bar region) for an in-bath and in-cell CNP. (C) Changes in electrical potential during a typical electrophysiology experiment showing both penetration and withdrawal of a CNP from the cell (arrows). Horizontal bars below the trace indicate the position of the CNP in relation to the cell as illustrated in (D). (D) Cross-section schematic illustrating the position of a CNP relative to the cell: (i) outside the cell; (ii) touching the cell membrane; (iii) forming a high resistance seal with the cell membrane; (iv) measuring the resting membrane potential; and (v) outside the cell.

In some embodiments, the probe is incorporated into an automated assembly that controllably inserts—via three-dimensional positioning—the probe into a subject. The insertion of the probe may be governed by comparison of the first electrical signal from within the subject to the second electrical signal measured from a reference exterior to the subject. As shown in FIG. 7, a change in electrical signal is evolved when the probe penetrates the boundary of the subject. Such an assembly may be a motor-driven positioning device. Single or multiple probes may be incorporated into a positioner device, which may in turn be used to effect simultaneous movement of multiple probes.

In some embodiments, the insertion is governed by measuring the potential difference between the conductive material residing within the subject and the electrical signal measured from the reference material exterior to the subject, as shown in FIG. 7. By monitoring the potential difference—or other signal—as a function of time and as a function of probe position, the user can determine when the probe has penetrated a boundary of the subject. This is useful in, for example, automated injection/monitoring systems, in which a system, such as a computer-controlled probe positioner, automatically locates cells and penetrates the cells with probes in order to monitor the cells, to inject the cells with a fluid or agent, or both. Such systems can be adapted to inject large numbers of cells simultaneously, thus enabling a large-scale study of cells or of other subjects, such as organelles, tissues, and the like.

Figure 5:
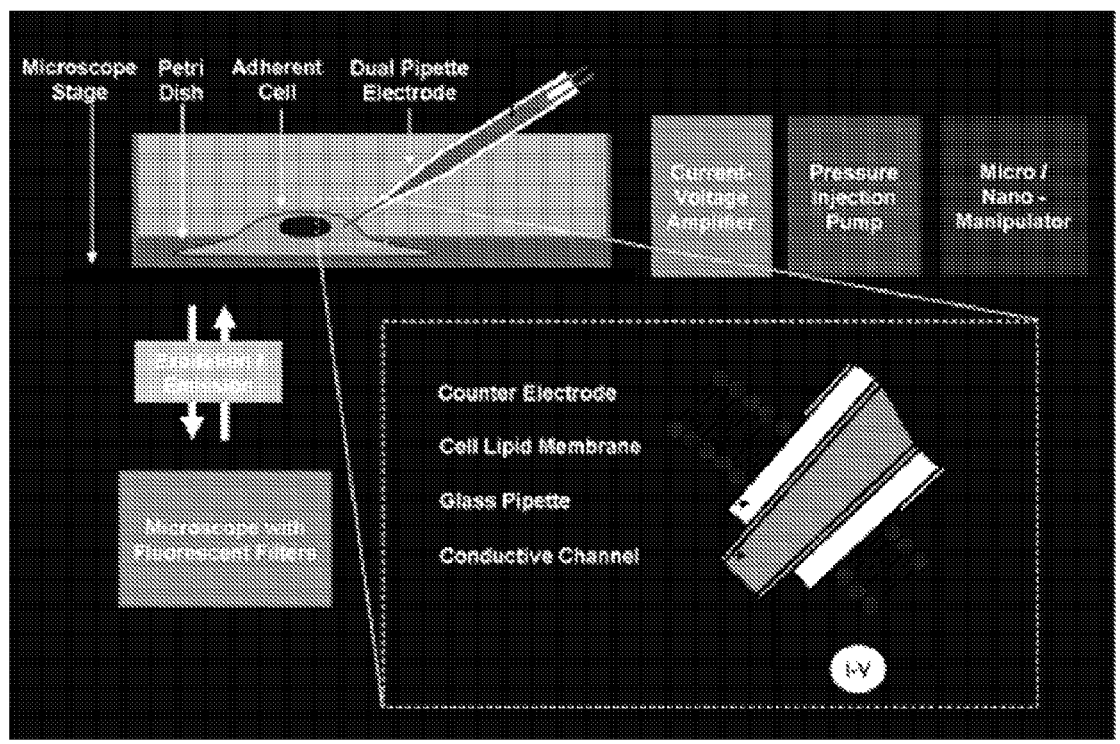
FIG. 5 illustrates an overall strategy for using the probe with multiple electrodes for concurrent pressure injection and electrical measurements.
Figure 6:
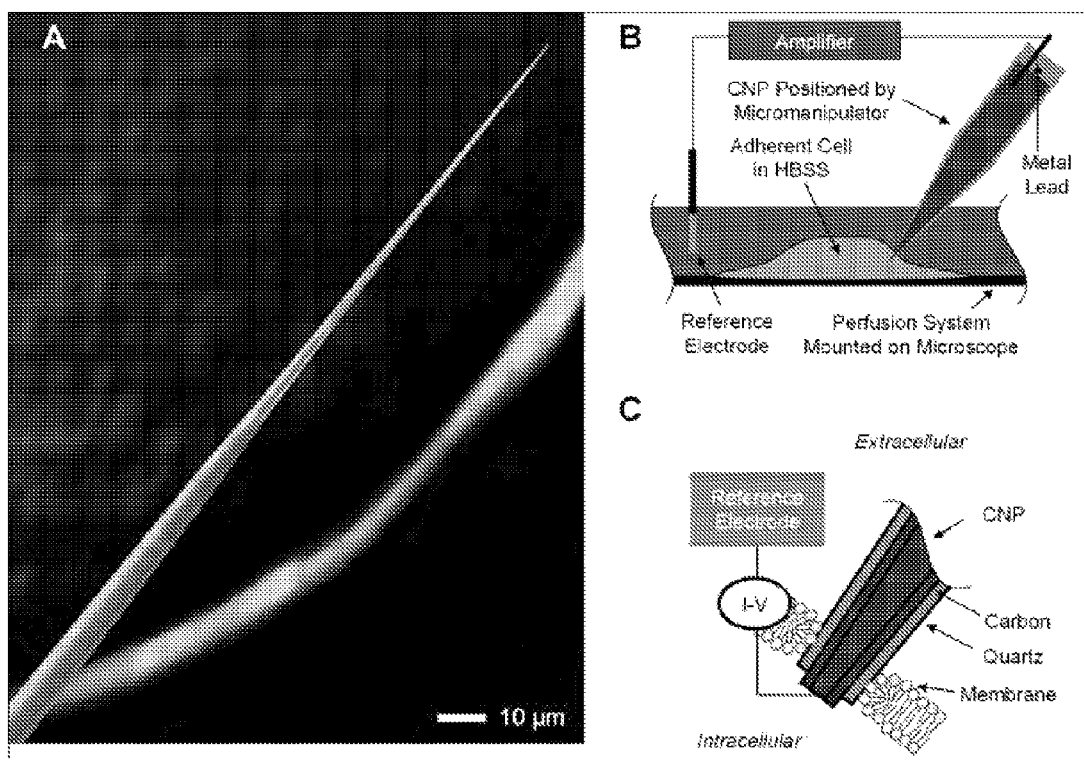
FIG. 6 depicts CNPs for electrophysiology. (A) SEM micrograph (IOKV) of a CNP tip. (B) Schematic detailing the experimental setup for CNP-based-electrophysiology. The CNP penetrates the cell and measures membrane potentials in current clamp mode vs. an Ag/Agcl reference electrode submerged in HBSS. (C) Cross-section schematic of a CNP and of the interface between the CNP and the cell membrane.

In some embodiments, monitoring of the first electrical signal is performed by the first conductive layer, as shown in, e.g., FIG. 5. In other embodiments, such as the embodiments shown in FIGS. 14, 15, and 16, the second conductive layer monitors the electrical signal from within the subject. The first electrical signal is suitably compared with a second—reference—signal, which signal may be collected from a reference buffer or other standard.

Figure 4:
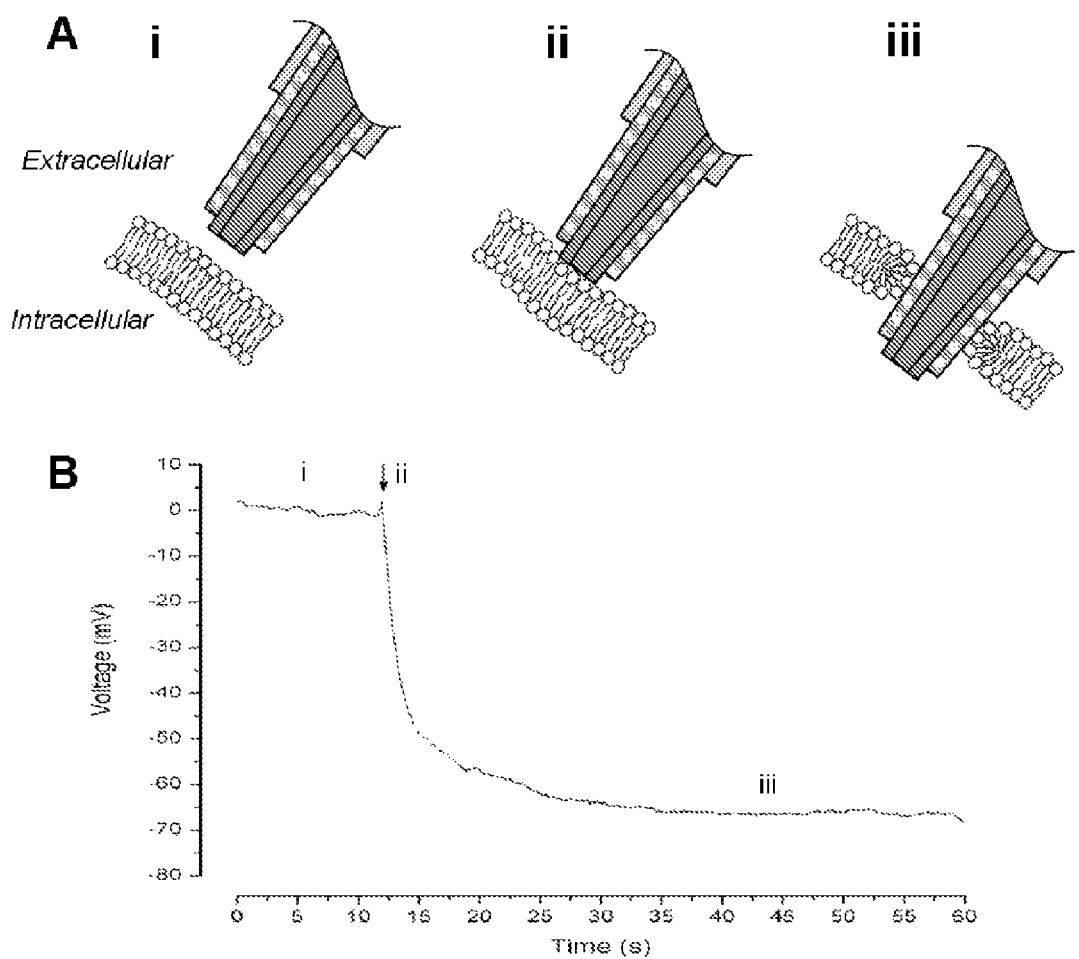
FIG. 4 illustrates electrically detection cell penetration. (A) Probe position relative to the cell as it approaches the cell (i), touches the membrane (ii), and measures the cell potential. (B) Actual voltage recording corresponding to the relative positions.
Figure 14:
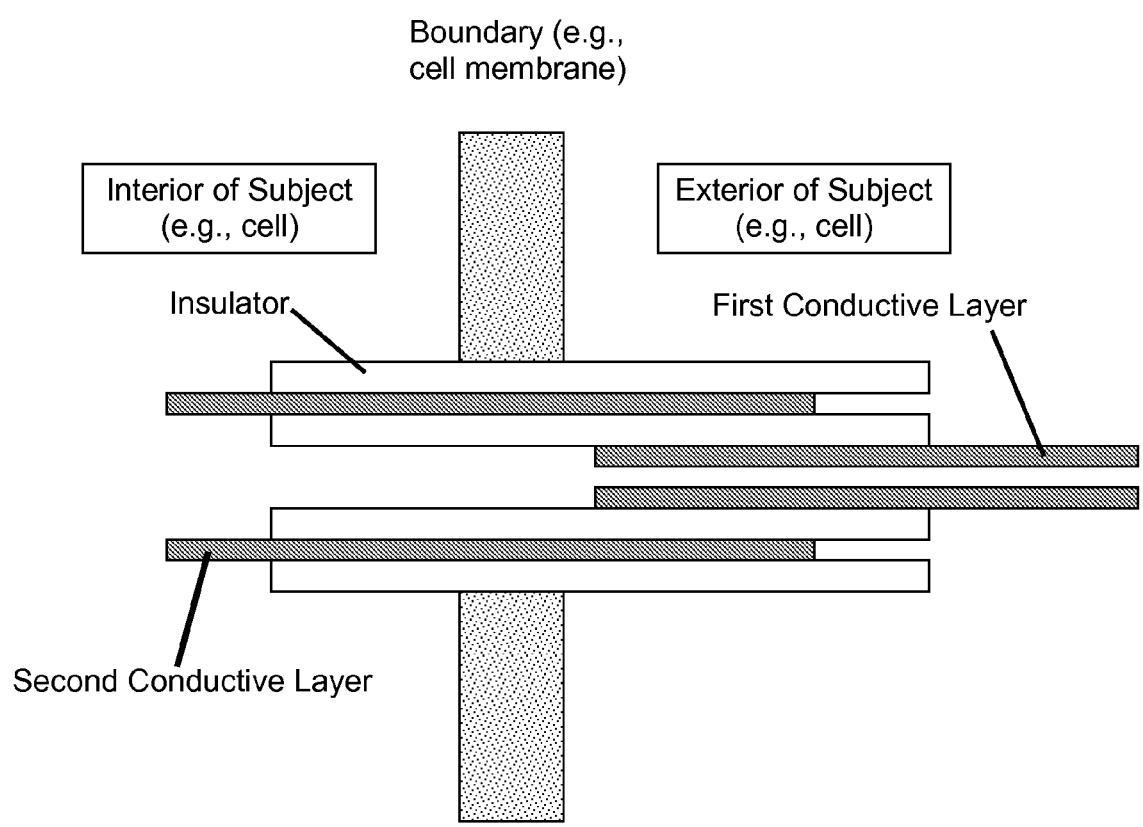
FIG. 14 illustrates an exemplary embodiment of the claimed invention, wherein the second conductive layer terminates beyond the distal end of the elongate insulator.
Figure 15:
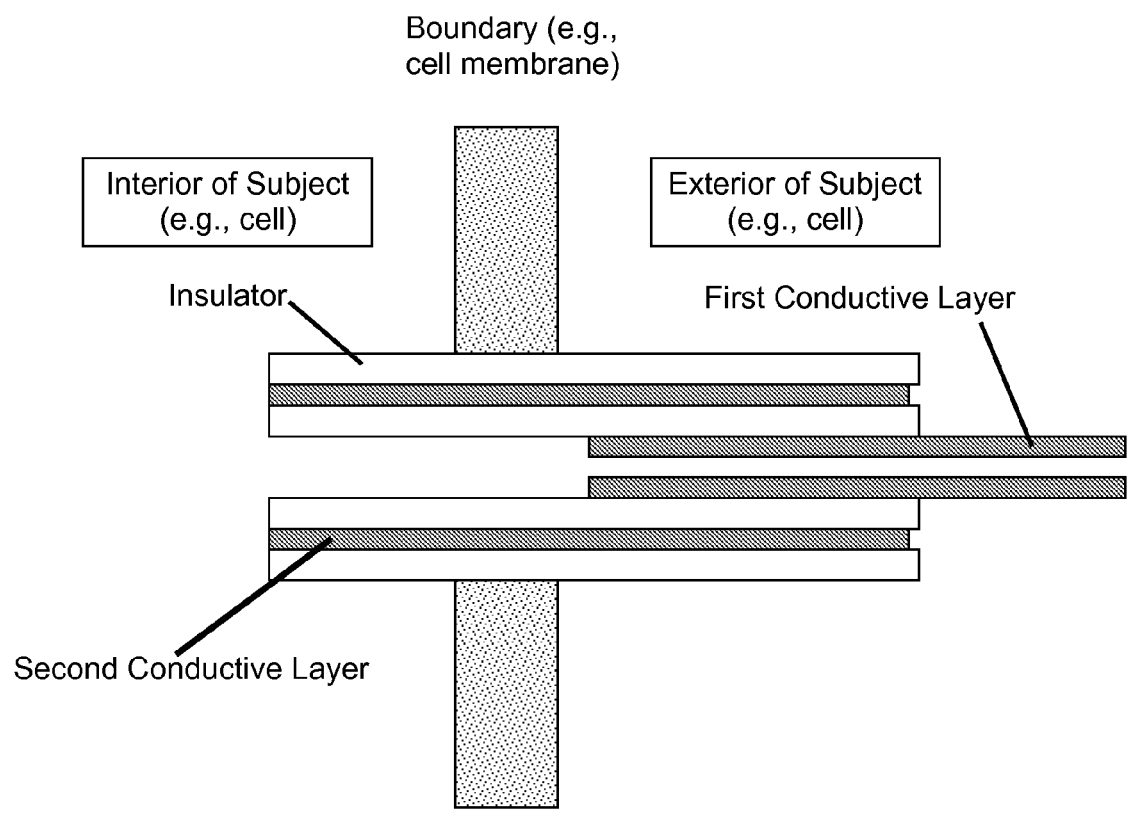
FIG. 15 illustrates an exemplary embodiment of the claimed invention, wherein the second conductive layer is essentially co-terminal with the distal end of the elongate insulator.
Figure 16:
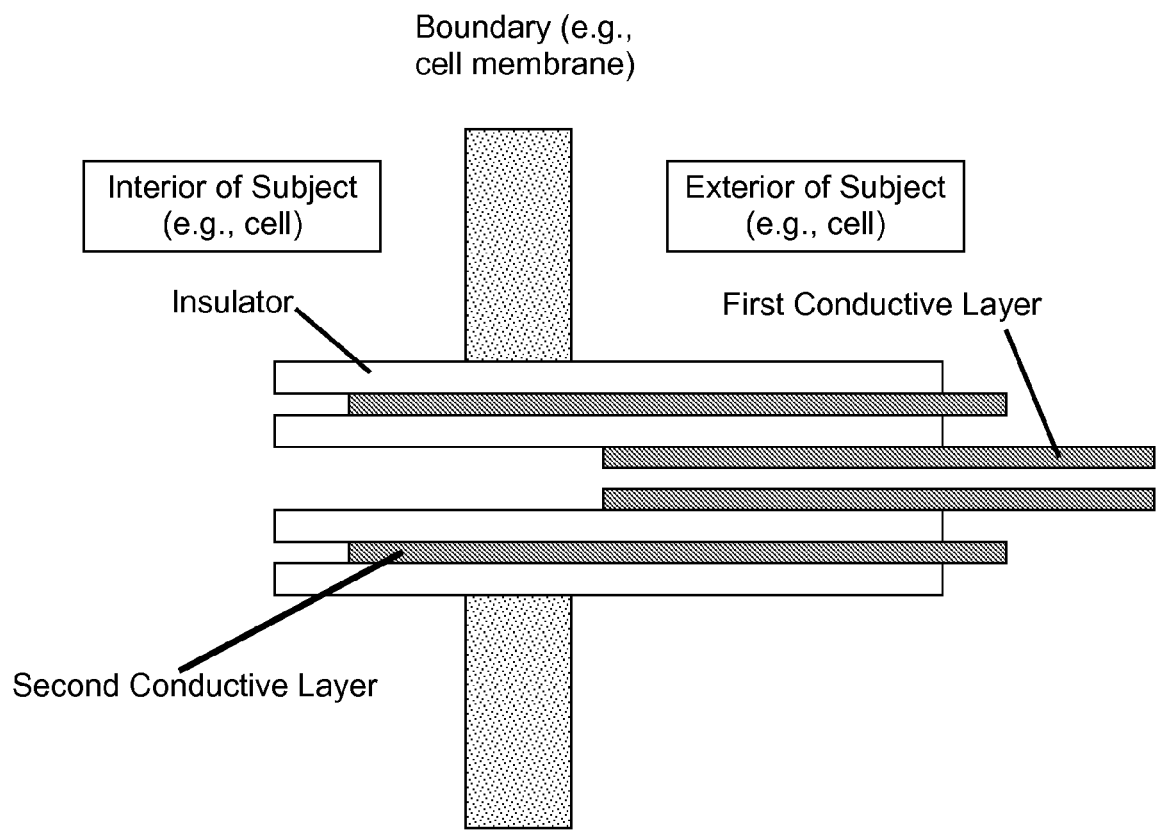
FIG. 16 illustrates an exemplary embodiment of the claimed invention, wherein the second conductive layer terminates at a location remote from the distal end of the elongate insulator.

The second electrical signal may be measured by the second conductive layer—as shown in FIGS. 4 and 5, or may be measured by the first conductive layer, as shown in FIGS. 14, 15, and 16.

In some embodiments, the methods include injecting a fluid into the cell. This is preferably accomplished by (once the probe has been inserted into the subject, e.g., FIG. 6), exerting/transporting the fluid across the lumen of the probe into the interior of the subject. Fluid injectors suitable for injecting appropriately small volumes of fluid will be known to those in the art and may include, for example, piezoelectric-based injectors.

Fluids injected into subjects may include tracers—including electrochemically active tracers—dyes (including fluorescent dyes), therapeutic compositions, toxins, preservatives, lysis agents, and the like. The methods may also include assaying the subject for the presence of the fluid or one of the fluid's components, or for the presence (or absence) of a composition that may be evolved from the presence of the fluid in the subject or from a reaction that may take place between the subject and a component of the fluid.

In some embodiments, the subject may then be assayed for the presence and quantity of a tracer or label present in the fluid, which presence and quantity may be used to determine the amount of fluid that was injected into the subject. Electrochemical signals—such as those evolved from an electrochemically active dye—may be monitored by one or more conductive layers. In other embodiments, a signal—electrical or electrochemical—is measured with an electrode deposited on the probe and a counter electrode, which is not attached to the probe.

The probes may, in some variations, include various suitable molecules, such as macromolecules, oligonucleotides, proteins, antibodies, and the like, as well as any combination thereof, can be attached as ligands to provide functionalized devices. These functionalized devices may suitably be used in biosensors or to extract or introduce material from a biological cell. Established chemistries known to those skilled in the art, for example, attaching biotin or avidin to carbon, can be readily adapted to attach ligands to the layers or insulators provided herein.

For example, when a probe comprises gold, there are well established linking chemistries, such as those involving sulfur, for attaching macromolecules such as proteins, oligonucleotides, antibodies, or any combination thereof to the gold. A variety of different types of measurements can be made using the biosensors. For example, the probes can be used to measure the I-V characteristics of electrolytes. The devices can also be used as proximity scanning probes based on electrochemical principles. The devices can also be used as a fabrication tool. The methods may be performed using probes according to the claimed invention; performance of the methods using probes having carbonaceous tips that are surmounted by a metallic layer is especially suitable.

Also provided are probes, the probes comprising an elongate insulator having a lumen, said lumen having a diameter of from about 1 nm to about 1 cm; a first conductive layer on the inner surface of the lumen and in electrical communication with a first contact; a second conductive layer surmounting at least a portion of the outer surface of the elongate insulator and in electrical contact with a second contact; and the first conductive layer and the second conductive layer disposed such that a portion of the first hollow insulator is surmounted by either the first electronically conductive layer or the second electronically conductive layer.

Exemplary probes are shown in FIGS. 1, 3, 4, and 11-13 (showing a probe where a portion of the elongate insulator is surmounted by only the first conductive layer) and FIGS. 14-16 (showing a probe where a portion of the elongate insulator is surmounted by only the second conductive layer). Suitable conductive and insulating materials are described elsewhere herein.

In some embodiments, at least a portion of the first conductive layer extends beyond one end of the elongate insulator. Carbon is especially suitable for use as a material for the first conductive layer, but metals and other conductors are suitable as well. The portion of the first conductive layer that extends beyond one end of the elongate insulator may be at least partially surmounted by a metal, as described elsewhere herein.

Further provided are probes, which probes include an elongate insulator having a lumen and a distal terminus, said lumen having a diameter of from about 1 nm to about 1 cm; a first conductive layer on the inner surface of the lumen and in electrical communication with a first contact; a second conductive layer surmounting at least a portion of the outer surface of the elongate insulator and in electrical contact with a second contact; and the first conductive layer and the second conductive layer disposed such that a portion of the first conductive layer or the second conductive layer extends beyond the distal end of the elongate insulator.

Figure 11:
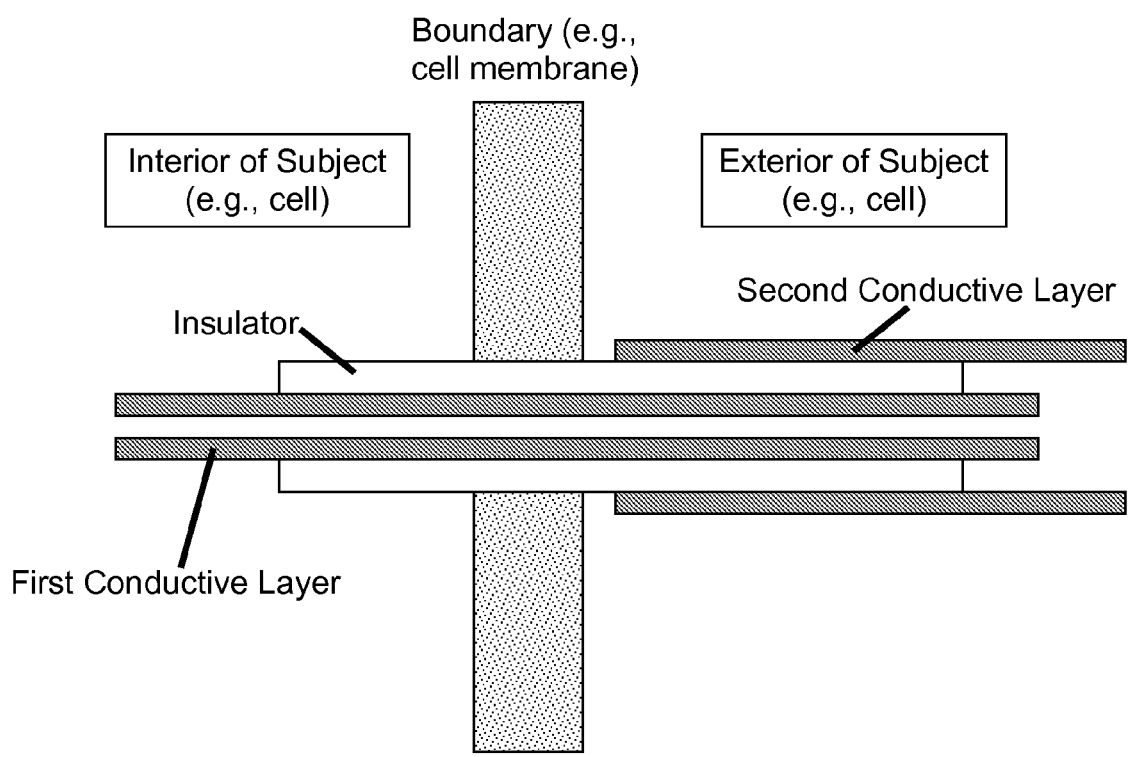
FIG. 11 illustrates an exemplary embodiment of the claimed invention; wherein the first conductive layer extends beyond the distal end of the elongate insulator.
Figure 12:
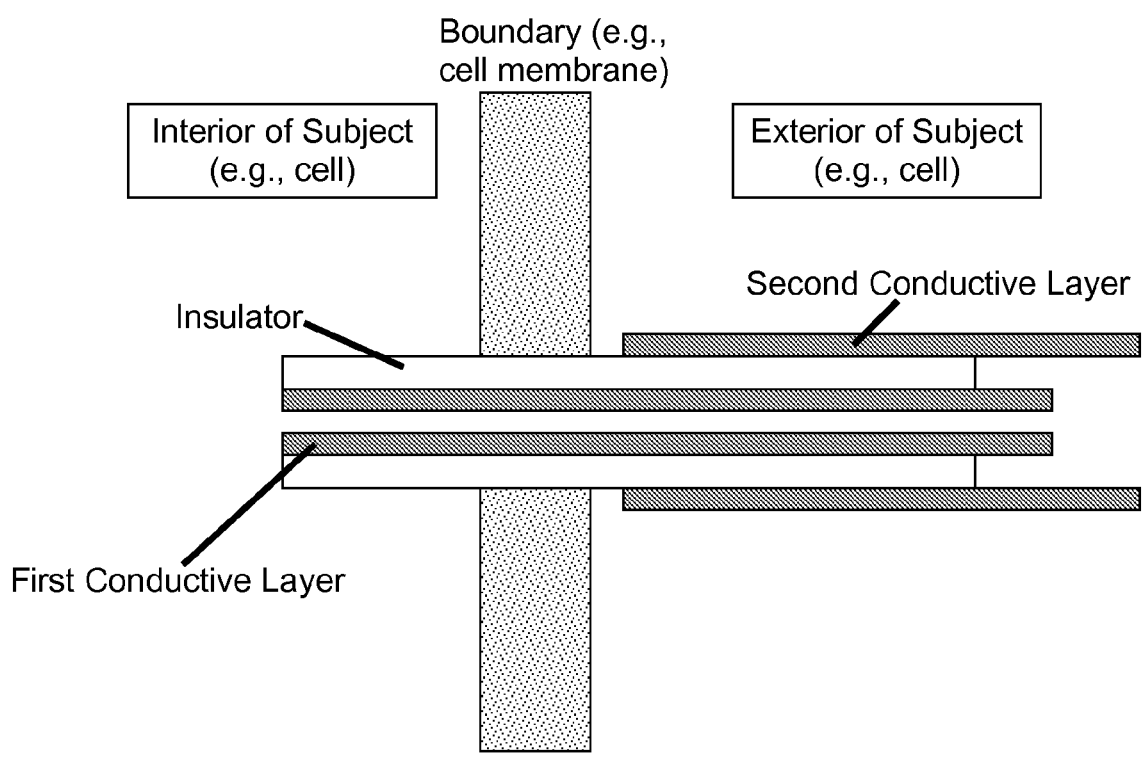
FIG. 12: Illustrates an exemplary embodiment of the claimed invention, wherein the first conductive layer is essentially co-terminal with the distal end of the elongate insulator.
Figure 13:
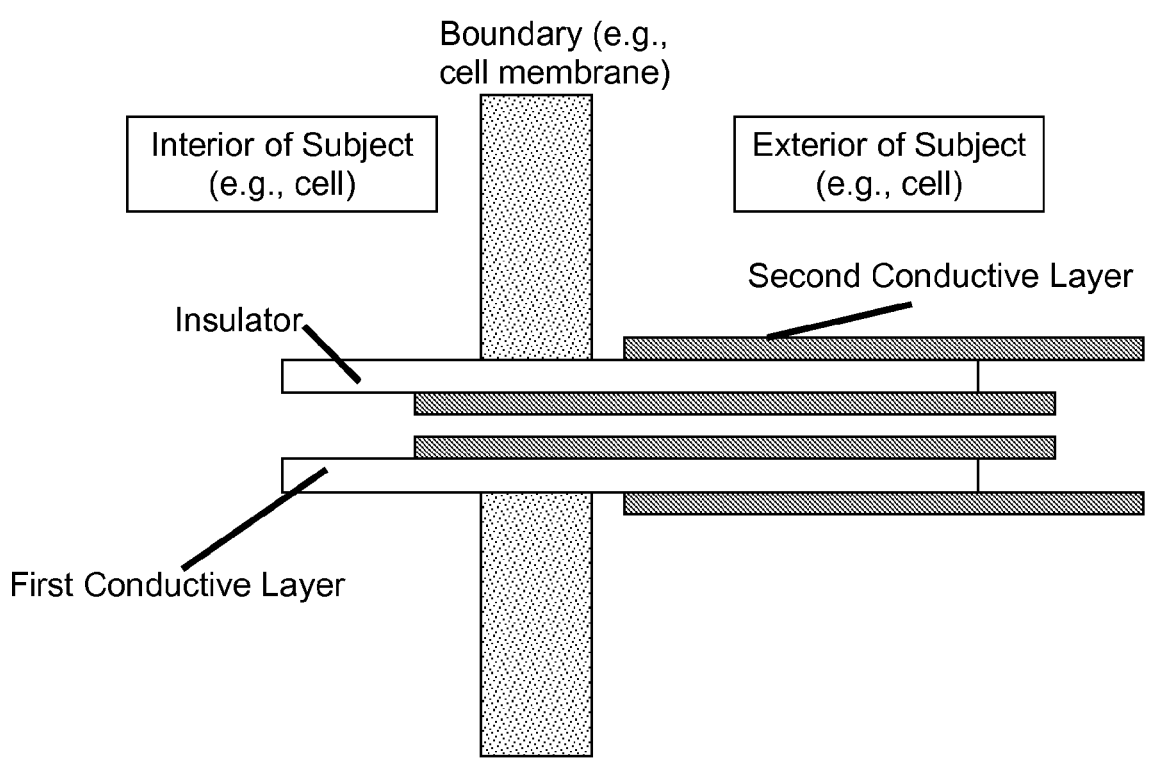
FIG. 13 illustrates an exemplary embodiment of the claimed invention, wherein the first conductive layer terminates at a location remote from the distal end of the elongate insulator.

Exemplary probes are depicted in FIGS. 1, 5, and 11 (showing first conductive layer extending beyond distal end of elongate insulator), and in FIG. 14 (showing second conductive layer extending beyond distal end of elongate insulator). Suitable conductive and insulating materials are described elsewhere herein.

As described herein throughout, the portion of the first conductive layer that extends beyond the distal end of the elongate insulator may be at least partially surmounted by a metal. The conductive layer may itself be carbon or a metal, and the surmounting metal may be silver, gold, platinum, and the like.

Additionally provided are methods of fabricating probes, the methods including disposing a first conductive layer along at least a portion of the inner surface of an elongate insulator having a lumen; disposing a second conductive layer along at least a portion of the outer surface of the elongate insulator; removing at least a portion of the elongate insulator, at least a portion of the first conductive layer, at least a portion of the second conductive layer, or any combination thereof, such that a portion of the elongate insulator is surmounted by either the first conductive layer or by the second conductive layer.

Suitable materials for the first and second conductive layers and suitable methods of disposition are set forth elsewhere herein.

Removal of a conductive layer or of the insulator suitably comprises contacting the elongate insulator, the first conductive layer, the second conductive layer, or any combination thereof, with an etchant, such as an acid. Other etchants will be known to those of ordinary skill in the art. In some embodiments, the etchant preferentially removes the second conductive layer relative to the hollow insulator. In other embodiments, the etchant preferentially removes the second conductive layer relative to the first conductive layer. The etchant may also preferentially removes the first conductive layer relative to the second conductive layer, or even preferentially remove the first conductive layer relative to the elongate insulator.

The etchant may be applied so as to expose at least a portion of the first conductive layer beyond the hollow insulator. The user may suitably electroplate a metal atop at least a portion of the portion of the first conductive layer exposed beyond the hollow insulator, and may also apply a halide ion to the electroplated metal so as to transform the electroplated metal to a metal halide. One exemplary embodiment of such a transformation is described in the examples section of the instant application, although other electroplating methods may be useful.

The present invention also provides methods of assessing the condition of a probe. These methods suitably include measuring the impedance between (A) an electrode disposed within a probe comprising (i) an elongate insulator having a lumen, said lumen having a diameter of from about 1 nm to about 1 cm, (ii) a first conductive layer on the inner surface of the lumen and in electrical communication with a first contact, (iii) a second conductive layer surmounting at least a portion of the outer surface of the elongate insulator and in electrical contact with a second contact, and (B) an electrode contacting a reference material exterior to the probe; and comparing the impedance to a reference value.

In this embodiment of the invention, the user may, for example, measure the impedance between an electrode inserted in the rear end of the pipette bore (without making contact with the carbon) and a reference electrode placed in a reference material (e.g., a buffer). The impedance is at least partially controlled by the nanosize opening at the distal end of the probe. This opening can, for example, be the opening at the end of the first conductive layer, as shown in FIG. 1.

Without being bound to any particular theory, an impedance measurement smaller than a predetermined value would indicate that the opening is too large, which oversize opening could be attributed to breakage or other damage to the probe. Alternatively, an impedance greater than a prescribed value suggests that the opening is narrower than desirable, which narrowness may be attributable to clogging.

In some embodiments, these methods may be integrated into a sensor or injector system, thus enabling identification (and replacement) of damaged probes.

Also provided are probes. These inventive probes include a hollow insulating handle comprising a first material, the handle comprising an exterior cross-sectional dimension of 500 microns at a point along the handle's length, and the handle suitably tapering to a distal end. The distal end of the handle has an interior cross-sectional dimension in the range of from about 10 nm to about 100 microns. The probes also include a capillary probe or fiber probe of a second material, said capillary or fiber probe conforming to at least a portion of the inner surface of the hollow macroscopic handle at the distal end, the second material being suitably a carbonaceous material, a metal, a semiconductor, or a combination thereof.

Figure 42:
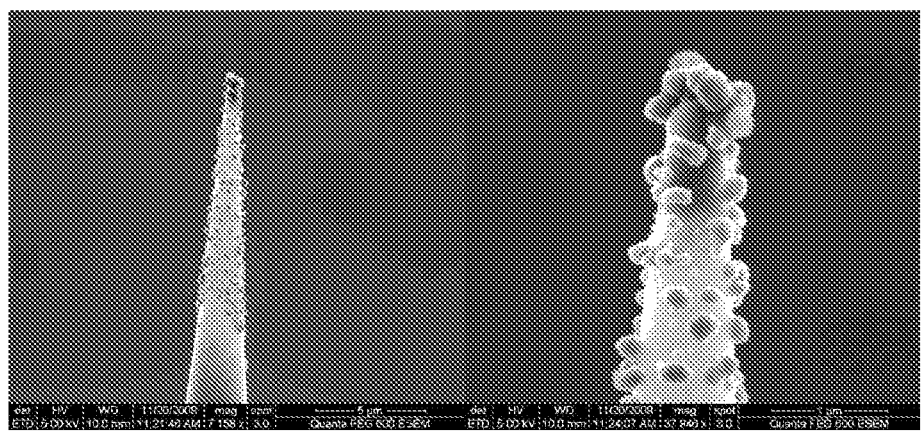
FIG. 42 illustrates SEM images of Ag-electroplated CNP under standard electroplating conditions. The electroplating solution is 1.0 mM $AgNO_3$+0.1M $KNO_3$. Double-pulse method is used: E1=−400 mV, t1=20 ms, E2=−30 mV, t2=2000 ms.

In some embodiments, a portion of the second material suitably extends beyond the handle, said portion of the second material extending beyond the handle being at least partially surmounted by a metal coating. Such a probe is shown in FIGS. 41 and 42.

Carbon is an especially suitable material for the second material. The metal coating suitably includes solver, gold, platinum, and the like. The metal coating may include a halide; silver chloride is considered an especially suitable coating. The coating thickness can be in the range of nanometers or even tens of nanometers. Coatings may even have thicknesses in the range of hundreds of nanometers, depending on the user's requirements.

Further provided are methods of fabricating probes. These methods includeexposing a portion of a conductive material beyond the terminus of an elongate insulator within which insulator the conductive material is disposed and electroplating at least a portion of the exposed portion of conductive material with a metal.

The conductive material may itself be carbon, as described elsewhere herein, as well as metals. The electroplating may be followed by contacting the electroplated conductive material with a halide solution. The methods may also, as described in additional detail in the examples section of the present application, include application of an ionic solution and a voltage so as to transform at least a portion of the deposited metal into a metal halide.

Additional Description

This invention describes novel probes consisting of multiple electrodes capable of concurrent material delivery and electrical signal measurement in contained volumes or cells, and the methods used to fabricate such devices.

The probes consist of two or more, independently insulated electrodes, made of any conducting material, on a single micro-/nano-sized probe. The electrodes are formed by depositing multiple conductive layers on glass templates, such as a glass micropipette, where each is separated by an insulating layer. The electrodes can be used as multiple individual working electrodes or reference, pseudo-reference, counter, or auxiliary electrodes. This enables the probe to singlehandedly measure electrical signals in fluid environments without the need for a second probe or other device to act as the reference electrode. The inventive technology offers a minimally-invasive, simple, and inexpensive alternative to traditional probes used for electrochemical analysis. Additionally, the technology offers a probe with multiple functions, such as injection and electrical measurement, for cell physiology.

The proposed probes with multiple electrodes have significant advantages over traditional methods using single electrode probes such as lower cost, smaller size, multifunctionality, concurrent electrical analysis, and potentially higher sensitivity. The embodiment of the probe takes advantage of a novel fabrication technique described in U.S. application Ser. No. 11/231,425 to incorporate conductive nanopipes into nanopipettes and nanoelectrodes without a need for assembly. The proposed sensors can be used for, among other things, cell biology, gene profiling, infectious diseases detection, and water and food supply monitoring.

Probes with multiple electrodes have several advantages over traditional electrodes such as smaller footprint, multi-functionality (injection and electrical measurement), reduced analytical complexity (one probe replaces many), and increased analytical efficiency (automated cell physiology). It appears that until now, there was no convenient way to fabricate multiple electrodes capable of probing cells.

The outer diameters of the nanopipes may range from tens of nanometers to a few microns. In one embodiment [FIG. 1], the probe with multiple electrodes consists of multiple conductive layers stacked on top of each other, each separated by an insulating layer, on a glass template. In another embodiment [FIG. 2], the probe with multiple electrodes consists of multiple electrodes at the probe's tip. Both probes can be used as stand-alone cellular probes to interrogate the interior of cells or analytical tools for detecting targeted analytes in solution. The probe is also multifunctional and can also act simultaneously as a multi-electrode sensor and nanopipette for the injections of proteins and genetic material into the cell's interior and for the extraction of molecules from the cell.

One embodiment of a probe with multiple electrodes consists of multiple conductive layers stacked on top of each other, each separated by an insulating layer, on a glass template. FIG. 1 depicts an example of a probe with multiple electrodes around a glass micropipette. Using a glass micropipette template, the first conductive layer is deposited along the entire length of the pipette's inner diameter. The second conductive layer is then deposited on the outside of the glass micropipette. The glass micropipette provides the insulation between the two conductive layers to produce a probe with two electrodes [FIG. 1A]. As shown in FIG. 1B, a probe with multiple electrodes is made by alternately depositing insulating and conducting layers on either the outer surface of the probe. Alternatively or coincidentally, layers can be deposited on the inner surface of the probe.

FIG. 1C illustrates the concept by showing an actual 2-electrode probe made from a quartz micropipette. The 2-electrode probe was made by first depositing a carbon layer (approximately 30 nm thick) along the entire inner diameter of inside the quartz micropipette using chemical vapor deposition (CVD). A titanium layer (approximately 100 nm thick) was then sputtered onto the outside of the quartz micropipette. The tip was then wet-etched in buffered hydrofluoric acid (6:1 BHF) for 2 minutes. The length of carbon exposed depends on the etching time. In this case, ~20 microns of carbon was exposed. However, the amount of titanium etched away from the tip depends on how far the probe tip was submerged into the BHF. In this case, the titanium layer was etched ~200 microns from the carbon tip. The resulting probe has a nanoscopic, hollow carbon electrode and a large-surface titanium electrode separated by a quartz insulating layer.

Another embodiment of probe with multiple electrodes at the probes tip. FIG. 2 depicts a probe with multiple electrodes at the tip of a glass micropipette with multiple bores. Using a glass micropipette with multiple bores [FIG. 2A-i], conductive layers are deposited on each of the bore's surfaces. Subsequent wet-etching in BHF removes the glass and exposes the multiple conductive tubes [FIG. 2A-ii]. Additionally, multiple electrodes can be deposited on the outside of the micropipette as described in the first embodiment to give rise to a device like that shown in FIG. 1.

FIG. 2B shows an example of a multiple electrode-tipped probe made from a multiple bored quartz micropipette. First, carbon was selectively deposited with CVD on the bore's surfaces of a multi-bore quartz micropipette. Then, the tip was dipped in BHF to remove the quartz and expose the carbon tips. FIG. 2B is a scanning electron micrograph of the resulting nanoscopic carbon tips. FIG. 2C demonstrates the flexibility of those tips when pressed against a hard surface.

Measuring Electrical Signals in Cells

The conductive properties of a probe with multiple electrodes also enable measurement of the electrical signals of cells. FIGS. 3A-B depict the overall strategy for measuring cell signals using probes with multiple electrodes, for example, a 2-electrode probe described in the first embodiment. The probe will be attached to an amplifier suitable for high-resistance electrodes. The probe may be maneuvered relative to an adherent cell in bath [FIG. 3A] so that one electrode pierces the cell membrane and another electrode remains outside the cell [FIG. 3B]. As shown in FIG. 3B, the smaller electrode which is inside the cell will be connected to the amplifier as a working electrode while the outside electrode will be utilized as a pseudo-reference electrode. In this manner, current and voltage can be measured across the cell membrane.

FIG. 3C is an actual voltage recording from a cell from a single electrode probe, fabricated with the methods described in the first embodiment. Using the strategy described above, a single electrode probe made of carbon pierced the cell and measured the cell membrane potential versus an Ag/AgCl reference electrode in bath (−55 mV). Upon briefly increasing the potassium ion concentration in the extracellular environment, the cell experiences a transient depolarization (membrane potential becomes more positive). FIG. 3C demonstrates the ability of the probes to measure the electrical signals of cells and suggests, with high probability, the capability of probes with multiple electrodes.

In a similar fashion, a probe with more than 2 electrodes, as described in either embodiment, can be maneuvered to pierce the cell so that multiple electrodes are inside the cell while one pseudoreference electrode remains outside (not shown). In this manner, multiple electrodes would allow one to perform electrochemistry inside the cell or independently yet simultaneously measure voltage and current across the cell membrane. Additionally, intracellular electrode surfaces consisting of different functionalizations enable targeted detection of various analytes within the cell.

Electrical Detection of Cell Penetration

The conductive properties of the probe make it possible to electrically detect when the probe comes in contact with the cell membrane or penetrates into the cell. FIG. 4A schematically depicts the relative position of a probe to the cell membrane as it approaches the cell [FIG. 4A-*i*], touches the cell membrane [FIG. 4A-*ii*], and successfully records stable measurements from the cell [FIG. 4A-*iii*]. FIG. 4B is an actual voltage recording from a cell from a single electrode probe, fabricated with the methods described in the first embodiment. From FIG. 4B, the probe is recording zero volts as it approaches a cell [FIGS. 4A&B-*i*]. As it makes contact with the cell membrane, the recorded potential increases approximately 4 mV just before it penetrates through [FIGS. 4A&B-*ii*]. After the cell membrane seals against the insulating exterior, the probe records a stable resting membrane potential (−66 mV).

At least two characteristics of penetrating a cell with the disclosed probes are useful for automated cell analysis. First, the slight increase in potential as the probe comes in contact with the cell membrane is useful in determining the probe's position relative to the cell. With the assistance, for example, of visual identification software, a probe may be automatically guided to a cell. In such a system, the probe is advanced until it made contact with the cell membrane, as in FIGS. 4A & B-ii. From that point, the probe is automatically advanced into the cell until a steep drop in potential was observed. A successful cell penetration is then confirmed by stable recording of the resting membrane potential of the cell, as in FIGS. 4A & B-iii. Following penetration, external equipment may be used to perform some type of task (e.g., injection) or the probe could be given a command to continue electrical measurement, inject fluid, or both simultaneously. These capabilities would allow automated cell probing, such as injection and electrophysiology.

Multifunctionality

The hollow configuration and conductive properties of probes with multiple electrodes make possible concurrent fluid injection and electrical measurement. FIG. 5 depicts one of the possible strategies for using multiple electrode probes for multiple uses. In FIG. 5, a 2-electrode probe is first connected to an electrophysiology amplifier and a pressure injection system. The probe is then maneuvered into a cell so that the smaller diameter, hollow electrode is sealed inside the cell while the other external electrode remains outside. Once the probe is successfully inside the cell, fluid can be injected and the cell response recorded simultaneously with a single probe.

The system may be configured such that injection is related to the cell's response to the injection. For example, the system might be configured to as to increase, decrease, or even cease injection when a certain cellular response is achieved. The user might also configure the system so as to withdraw material from within the cell when a certain response is detected. The system might also be configured to inject a second agent into a cell when the cell's response to a first agent is detected or reaches a certain level.

A multi-electrode probe which replaces the tasks of many is advantageous for several reasons. First, multi-electrode probes offer cell probing capabilities that are currently not available, such as intracellular electrochemistry and concurrent injection and electrophysiology. Second, integrating multiple cell physiology techniques requires the skills of highly trained personnel to perform time consuming and technically demanding experiments. Replacing the many probes with one, multipurpose probe will reduce experimental complexity, decrease result variability, and reduce experimental time and cost by increasing experimental efficiency. Third, the combined properties of hollow, multi-electrode probes enable automated cell physiology.

Non-Limiting Embodiments and Additional Experimentation

The ability to monitor living cell behavior in real time and with high spatial resolution is vital for advancing knowledge of cellular machinery and evaluating cellular response to various drugs. Described below is the use of carbon nanopipettes (CNPs) made according to the claimed invention, which integrate carbon nanopipes into the tips of pulled glass capillaries, to measure electrical signals in the mouse hippocampal cell line HT-22. Using a standard electrophysiology amplifier in current-clamp mode, resting membrane potential of cells and their transient membrane response to extracellular pharmacological agents were measured. In addition to their superior injection capabilities reported previously, CNPs are capable of multifunctionality, enabling, for example, concurrent intracellular injection and electrical measurements without damaging cells.

Cellular probes designed to monitor electrophysiological events play a crucial role in experimental cell biology and pharmacology. In modern electrophysiology, electrolyte-filled glass micropipettes are utilized to access intracellular domains in order to measure how a stimulus affects the flow of ions through or changes the electrical potential across the cell membrane. Traditionally, electrical measurements in small cells are measured with either large-tipped, glass micropipettes filled with intracellular solution (2-3 pm OD, patch-clamp technique) or fine-tipped, glass micropipettes filled with highly concentrated salt solution (<1 pm OD, sharp microelectrode technique). Although very versatile and widely-used, the patch-clamp technique ruptures the cell membrane and alters the internal milieu of a cell, preventing long term and/or repetitive monitoring. In contrast, fine-tipped, glass microelectrodes are less intrusive and therefore are more likely to spare a cell from irreparable damage. However, cell damage may still occur during prolonged measurement when the high concentration electrolyte contained in the pipette's lumen diffuses into the cell. Problems that plague both intracellular recording techniques and inevitably degrade recording performance include clogging of the electrode tip, collecting debris at the tip during probe penetration, and damaging the tip upon approaching and penetrating the cell. Existing technologies preclude independent electrical measurement of physiological responses during concurrent injection of molecules.

CNP cellular probes, in particular, have shown superior performance over their glass counterparts. As previously reported, CNPs could penetrate cells and inject calcium-mobilizing second messengers without compromising cell viability and with fewer instances of tip clogging and breakage. To investigate cell electrophysiology, standard system was utilized, depicted schematically in FIG. 6B, consisting of an electrophysiology amplifier, a micromanipulator, and an upright microscope with a water-immersion lens. Once the CNP was affixed to the amplifier headstage, its conductive carbon tip could penetrate the cell membrane to provide a nanoscale electrical conduit for accessing the intracellular environment [FIG. 6C].

To demonstrate the feasibility of carrying out electrophysiological measurements with CNPs, resting membrane potential (RMP) of the mouse hippocampal cell line HT-22 was measured and the subsequent potential variations caused by adding pharmacological agents to the cell bath. Mammalian cells can exhibit RMPs ranging from −30 to −75 mV as a result of ion concentration differences between the intra- and extracellular domains. The electrical potential across the cell membrane can be estimated by considering the concentration differences of membrane-permeant monovalent ions using the Goldman equation, $$E_m = \frac{RT}{F} \ln\left(\frac{P_{K^+}[K^+]_o + P_{Na^+}[Na^+]_o + P_{Cl^-}[Cl^-]_o}{P_{K^+}[K^+]_i + P_{Na^+}[Na^+]_i + P_{Cl^-}[Cl^-]_i}\right), \quad (1)$$

where R is the ideal gas constant, T is the temperature, F is the Faraday constant, iq, is the permeability of the ion, and $[ion]_o$, and $[ion]_i$ are, respectively, the concentrations of the ion outside and inside the cell. Since membranes of mammalian neurons are significantly more permeable, under normal conditions, to potassium ions than sodium ions and chloride ions, the Goldman equation simplifies to the Nernst equation, $$E_{m,K^+} = \frac{RT}{F} \ln\left(\frac{[K^+]_o}{[K^+]_i}\right). \quad (2)$$

Using the Nernst equation, an estimation of a cell submerged in Hank's Balanced Salt Solution (HBSS) ($[K^+]_o/[K^+]_i$, =6 mM/130 mM) at room temperature (20° C.) would have a K+-governed membrane potential of roughly −78 mV. By introducing pharmacological agents to the cell bath that modify the intracellular and extracellular ion concentrations, the cell membrane potential may be altered, and the variations measured with CNPs.

Experimental Results

Intracellular Recording with Carbon Nanopipettes. FIG. 7A shows a typical CNPmeasured voltage (−50 mV) in response to a small square current pulse of −10 pA when the CNP is immersed in the HBSS. The corresponding effective resistance (5 GOhm) is attributed to the extremely small area of the carbon surface exposed to the solution and the need to overcome the solid-liquid junction impedance. By fitting the response lag with an exponential decay for an RC circuit, it is estimated that the system has an effective capacitance of 200 pF with a time constant of 660 ms.

Next, it was assessed whether CNPs were capable of measuring the membrane potentials of cells with stability and low drift during a long-time recording. FIG. 7B illustrates the probe behavior of a CNP electrode during in-bath and in-cell voltage recordings over several minutes. As indicated in FIG. 7B (horizontal bar region), the in-bath and in-cell CNP recordings have negligible drift over several minutes. Although negligible drift is typical, drift was observed on occasion as high as 1.25 mV/min in the negative direction. Over the several minutes after penetrating HT-22 cells, CNPs measured RMPs of −61.5 mV k 2.97 mV (mean±s.e.m.; n=26) from stable signals with noise ranging from 1.1-1.6 mV rms.

FIG. 7C shows CNP-measured potential variations as a function of time as a CNP approached, penetrated, and withdrew from an HT-22 cell. FIG. 7D schematically depicts the position of the CNP relative to the cell. Regions (i)-(v) in FIG. 7C are cross-referenced with the CNP positions in FIG. 7D. Once the CNP was lowered into the bath solution and approached the adherent cell, the CNP potential was nulled [FIG. 7C-D (i)]. Before cell penetration, a slight potential increase (+5 mV) indicated close approach and contact between the CNP and the cell membrane [FIG. 7C-D (ii)]. When the CNP penetrated the cell membrane, as indicated by the arrow in FIG. 7C, there was a steep drop in the potential. As the ruptured cell membrane formed a high-resistance seal with the quartz exterior of the CNP [FIG. 7C-D (iii)], the voltage drop asymptoted and became nearly level after approximately 3 seconds. A successful CNP current-clamp was evident upon measuring a stable RMP ($E_{RMP}$=−35 mV) [FIG. 7C-D (iv)]. After a short but successful current-clamp, the CNP was withdrawn from the cell, as indicated by the arrow in FIG. 7C, and the potential returned to its extracellular value of zero [FIG. 7C-D (v)].

Recording Cellular Responses to Ionic Enrichment.

Because the cell membrane is highly permeable to potassium ions (K+), an increase or decrease in extracellular K+ concentration will, respectively, cause a resting cell to depolarize (membrane potential becoming more positive) or hyperpolarize (membrane potential becoming more negative). Utilizing CNPs, variations in membrane potential were monitored over tens of minutes. FIG. 8A is a recording of membrane potential from an HT-22 cell during perfusion intervals with normal HBSS and K+-enriched HBSS (additional 5 mM K+). Subsequent to penetrating the cell with a CNP and measuring a stable RMP under normal HBSS perfusion ($E_{RMP}$, =−72 mV), the cell was perfused with K+-enriched HBSS which resulted in a 15 mV depolarization. After approximately 2 min at higher extracellular K+, the cell was perfused with normal HBSS and the cell slowly returned to its RMP.

Next, a CNP was used to measure changes in membrane potential during repetitive extracellular administration of KCl [FIG. 8B]. After penetrating the cell, as indicated by the arrow in FIG. 8B, the CNP measured a stable RMP under normal HBSS perfusion (Emp=−68 mV). Adding KCl to the cell bath (additional 25 mM K+) produced a transient, K+-enriched HBSS environment which resulted in a 40 mV depolarization. Under constant perfusion in normal HBSS, the membrane potential returned to its original value after −30 sec. The results were reproducible with high fidelity.

FIG. 8C is a representation of potential variations as a function of time during the administration of HBSS and the varied K+-enrichment of HBSS (additional 5 and 15 mM K+). As expected and illustrated in FIG. 8C, the addition of normal HBSS did not change extracellular K+ concentration and therefore did not affect the RMP ($E_{RMP}$, =−57 mV). In contrast, adding KCl to the cell bath (additional 5 mM K+)

produced a transient, K+-enriched HBSS environment which resulted in a 10 mV depolarization. As normal HBSS perfusion brought the bath back to its initial K+ concentration, the cell returned to its RMP in ~90 seconds. Likewise, adding more KCl to the cell bath (additional 15 mM $K^+$) resulted in a 30 mV depolarization before returning to its RMP in ~90 seconds.

Figure 9:
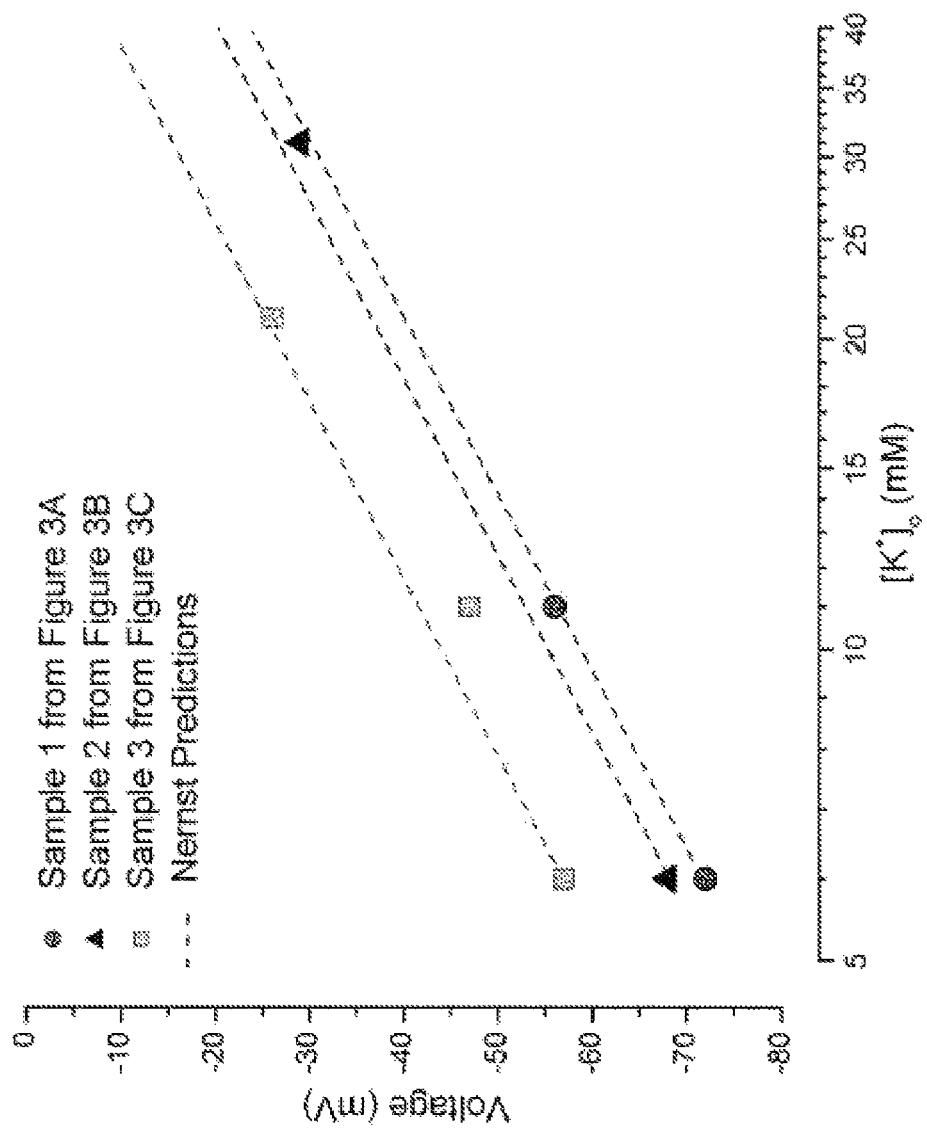
FIG. 9 illustrates CNP-recorded membrane potentials of HT-22 cells as functions of the extracellular K+ concentration. The various symbols and lines represent cells, in HBSS having different RIVIPs. The symbols and lines correspond, respectively, to experimental data and predictions based on the Nernst equation.

The membrane potentials of HT-22 cells over various extracellular K+ concentrations were consistent with predictions based on the Nernst equation. FIG. 9 compares the experimental data (symbols) measured with CNPs and Nernst predictions (dotted lines) of cell membrane potentials as a function of extracellular K+ concentration. The various symbols and lines represent cells in HBSS having different RMPs. CNP-recorded RMPs of HT-22 cells were in agreement with the K+-governed membrane potentials predicted by the Nernst equation ($E_{m,K+}$=−78 mV). Moreover, CNP-measured potential variations due to changes in extracellular K+ concentration were in good agreement with Nernst predictions.

Recording Cellular Responses to Pharmacological Stimuli.

In addition to monitoring predictable cell membrane potential changes caused by ionic enrichment, CNPs were utilized to electrically record cell responses to pharmacological stimuli. Y-aminobutyric acid (GABA), a principal inhibitory neurotransmitter in the mammalian central nervous system which acts as an agonist for the membrane-bound GABAA receptor, was administered. When GABA binds to the GABAA receptor, the cell hyperpolarizes as a result of Cl-ion influx due to the opening of the ligand-gated Cl-ion channel. However, the hyperpolarization can be blocked by perfusing cells with bicuculline (BIC), a competitive antagonist for the GABAA receptor which binds to the GABAA receptor and prevents it from opening even in the presence of GABA. Several reviews detailing these mechanisms exist.

Figure 10:
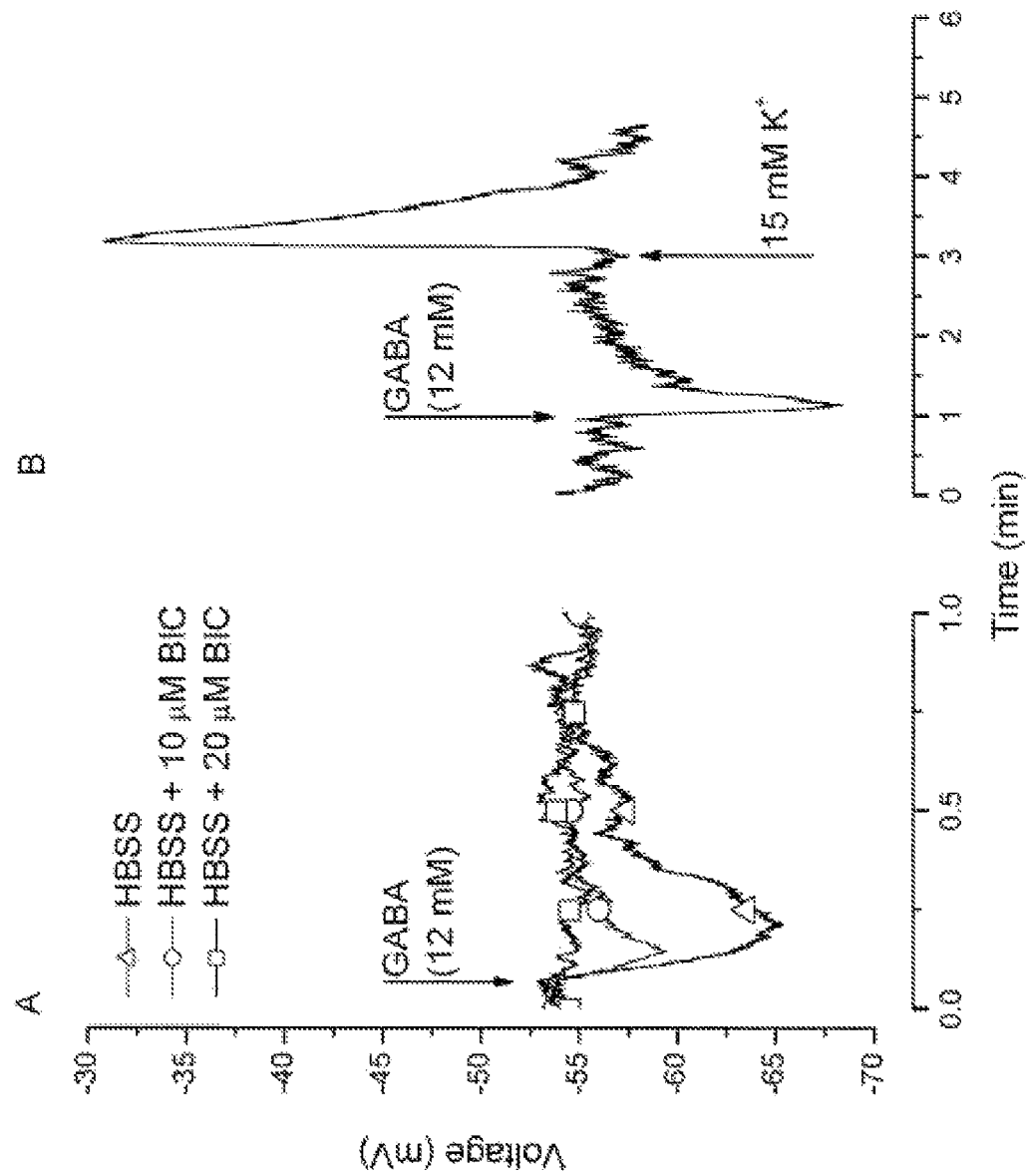
FIG. 10 illustrates CNP-recorded variations in membrane potential during pharmacological stimulation. (A) Variations during the administration of GABA (12 mM, arrow) to HT-22 cells perfused in normal HBSS (black triangles), HBSS and 10 µM BIC (red circles), and HBSS and 20 µM BIC (blue squares). (B) Variations over time during the administration of GABA (12 mM, arrow) and the K+-enrichment of HBSS (additional 15 mM $K^+$)

FIG. 10A illustrates how an HT-22 cell responded when GABA was added to the cell bath (12 mM GABA in bath, arrow). The addition of GABA resulted in a 10 mV hyperpolarization (black triangles) from the RMP ($Em_{RMP}$=−53 mV). Under constant HBSS perfusion, the cell returned to its RMP in 30 sec. In contrast, as demonstrated in FIG. 10A, administering GABA to the same cell pretreated with bicuculline (BIC, 10 μM) resulted in a 5 mV hyperpolarization (red circles). The hyperpolarizing response to GABA was completely blocked (blue squares) by perfusion of BIC at a higher concentration (20 μM).

Lastly, CNPs were used to electrically record a cell response to sequential pharmacological stimulation and ionic enrichment. FIG. 10B represents the opposing membrane responses to such stimuli over time. The extracellular administration of GABA (12 mM GABA in bath, arrow) resulted in a 12 mV hyperpolarization from its RMP ($E_{RMP}$=−57 mV). Once the GABA was washed away under constant HBSS perfision, the cell returned to its RMP in 60 sec. Following stabilization, the addition of KCl to the bath (additional 15 mM K+) produced a transient, K+-enriched HBSS environment which resulted in a 25 mV depolarization. As excess KCl was washed away under constant HBSS perfusion, the cell returned again to its RMP after 60 sec.

Methods and Materials

CNP Fabrication.

CNPs were fabricated using processes described previously [10]. Briefly, catalyst-laden quartz capillaries were first pulled into fine-tipped, blunt taper micropipettes. Next, the micropipettes were subjected to a chemical vapor deposition process which selectively deposits a carbon film along the entire length of the inner catalyzed surface. The thickness of the film was controlled by adjusting the deposition time. The tips were then dipped in buffered hydrofluoric acid at room temperature for 30 sec to expose a very short length (<1 μm) of the interior carbon nanopipe. Hundreds of CNPs with tip outer diameters ranging from 200 to 400 nm (30 nm wall thickness) were fabricated concurrently without a need for any assembly. FIGS. 6A and 1C are, respectively, a micrograph and a schematic depiction of the CNP.

Cell Culture and Preparation.

The mouse hippocampal cell line HT-22 was kindly provided by Dr. David Schubert (The Salk Institute, San Diego, Calif.). Cells were grown in Dulbecco's Modified Eagle Medium (DMEM, high glucose) supplemented with 10% fetal bovine serum (FBS) and 1% antibiotics. The cells were plated on 12 mm cover slips 48 hrs prior to the electrophysiology measurements. The cells on the cover slips were incubated in HBSS (with calcium and magnesium) at room temperature for 10 min prior to measurements. The cover slips were subsequently placed in an open diamond perfision bath (Warner Instruments Corp., RC-22C) positioned on an upright microscope (Nikon eclipse E600FN, 40× water-immersion lens, Burleigh Gibraltar fixed-stage platform) located atop a vibration-isolation table. Cells were routinely perfised with HBSS at a flow rate of 1.0 ml/min.

Electrophysiology.

Membrane potential measurements were recorded with an Axon AxoClamp-2A amplifier equipped with a headstage for high resistance electrodes (Axon HS2-XO.OlMU) and Digidata 1322A digitizer (Axon Instruments/Molecular Devices, Sunnyvale, Calif.). Experimental protocols were controlled and data acquired by a personal computer using the Clampex 8.2 software (Axon Instruments). CNPs were inserted into a standard electrode holder until the metal wire of the holder came in contact with the inner carbon film of the CNP. A slight positive pressure was applied through the holder's perfixion port to keep external solution from filling the hollow CNP by capillarity. A micromanipulator (Narishige MHW-3) was used to manipulate and position the CNP electrodes during the electrophysiology measurements. All the electrical measurements were carried out versus an AglAgCl reference electrode submerged in HBSS in discontinuous current clamp @CC) mode, at zero current, with no capacitance compensation. The CNP potential was nulled (+I-2 mV) with the amplifier offset potential during immersion in HBSS before all electrical measurements. Recorded electrical measurements were not adjusted to compensate for differences in extracellular and intracellular junction potentials.

Chemicals.

Potassium chloride (KCl), (−)-Bicuculline methiodide (BIC), and yaminobutyric acid (GABA) were purchased from Sigma Chemical Co (St. Louis, Mo.). Hank's balanced salt solution (HBSS, with calcium and magnesium, ~6 mM $K^+$) was purchased from HyClonelThermal Fischer Scientific, Inc. (Logan, Utah).

Additional Embodiments

Counter Electrodes

Provided below is additional information regarding fabrication of probes and other devices having counter-electrodes.

As described generally herein, the fabrication process consisted of pulling quartz capillaries with 1 mm nominal diameter to form injection-type pipettes [Schrlau M, Nanotechnology, 19, 015101] and depositing a thin film of carbon along the inner surface of the quartz capillary. One exemplary process is described in U.S. patent application Ser. No. 11/231, 425, the entirety of which is incorporated herein by reference for all purposes. The deposition process lasted about three hours to form a carbon film with approximate thickness of 60 nm. Both un-etched and etched injection type CNPs were coated with metal.

To develop the method of coating counter electrodes on the outer surface of the glass, titanium was selected for the present, non-limiting embodiments. Silver and other conductive metals are also considered suitable, and may be used in conjunction with sputtering techniques.

Ti layers with thicknesses of 40 nm and 100 nm were deposited on the outer surface of CNPs using a Emitech k575x turbo sputter dual head system. Five minutes deposition resulted in ~40 nm thick layer and ten minutes deposition resulted in about 100 nm thick layer. To obtain a homogenous Ti layer, the CNPs were rotated midway during the sputtering process. The counterelectrode layers may have thicknesses of tens or even hundreds of nanometers. A counterelectrode having a thickness of a micron or even 5 or 10 microns is also within the scope of the claimed invention. Thin counterelectrodes are considered especially suitable, as thin counterelectrodes enable the user to make use of the thin profile of the devices.

To effect a CNP tip free of Ti, Since we wish the CNP's tip to be free of Ti, chemical etching was used to remove the Ti layer from the CNP's tip. The etchant was a diluted HF buffer solution (1:100, Transens). The HF buffer solution was overlaid with mineral oil layer to decrease the BHF capillary rise along the outer surface the CNP, to maintain a better control of the etching length, and to prevent vapor-induced etching above the liquid-air interface. The etching length was controlled by adjusting the submersion depth of the tip in the etchant.

To control the CNP's immersion depth in the BHF solution, a Pt wire was placed in the BHF solution to serve as an electrode and the electric current between the titanium and platinum electrode (wire) was monitored. The Ti-coated CNP was mounted on an arm of a computer-controlled micromanipulator (Eppendorf Transferman NX7) and the titanium coating was electrically connected to a patch clam amplifier (HEKA).

A potential difference of about 5 mV was applied between the titanium coating and the Pt electrode and the electric current was monitored as a function of time. When the CNP was outside the BHF, there was no conductive path between the titanium and the Pt electrode and no electric current was registered. The CNP was lowered slowly into the BHF solution at increments of 1-5 μm per step of the manipulator's stepper motor; the electrical motor converts electrical pulses triggered by rotation of the joystick into discrete mechanical movements.

Once the titanium coating made contact with the BHF, the BHF solution provided a conductive path between the titanium and the Pt electrode and electric current was registered. The appearance of electric current signaled that the titanium coating made contact with the BHF solution. If desired, the CNP is then be further lowered into the buffered HF solution to a pre-determined depth with the micromanipulator to etch some of the titanium coating. The disappearance of the electric current indicated that the submerged titanium layer was completely etched. The monitoring of the electric current provides a means to automate the etching process. The titanium electrode was examined with a scanning electron microscope (SEM, FEI Quanta FEG ESEM) subsequent to the etching process.

Results and Discussion

Ti Sputtered Layer

Figure 17:
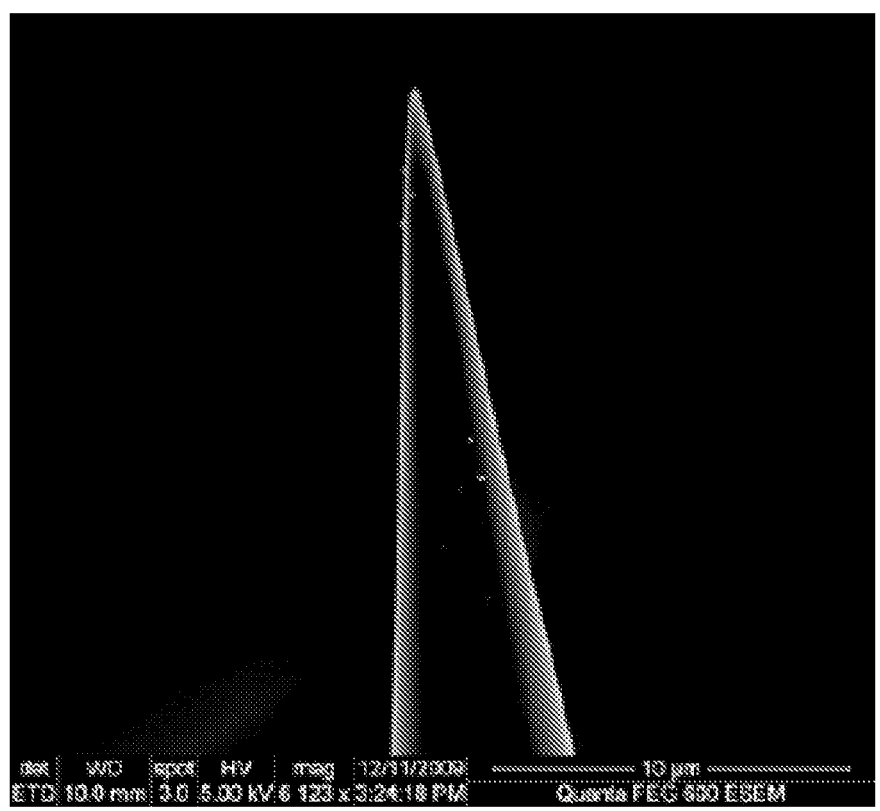
FIG. 17 illustrates a SEM image of the tip of a CNP coated with Ti (40 nm thickness)
Figure 18:
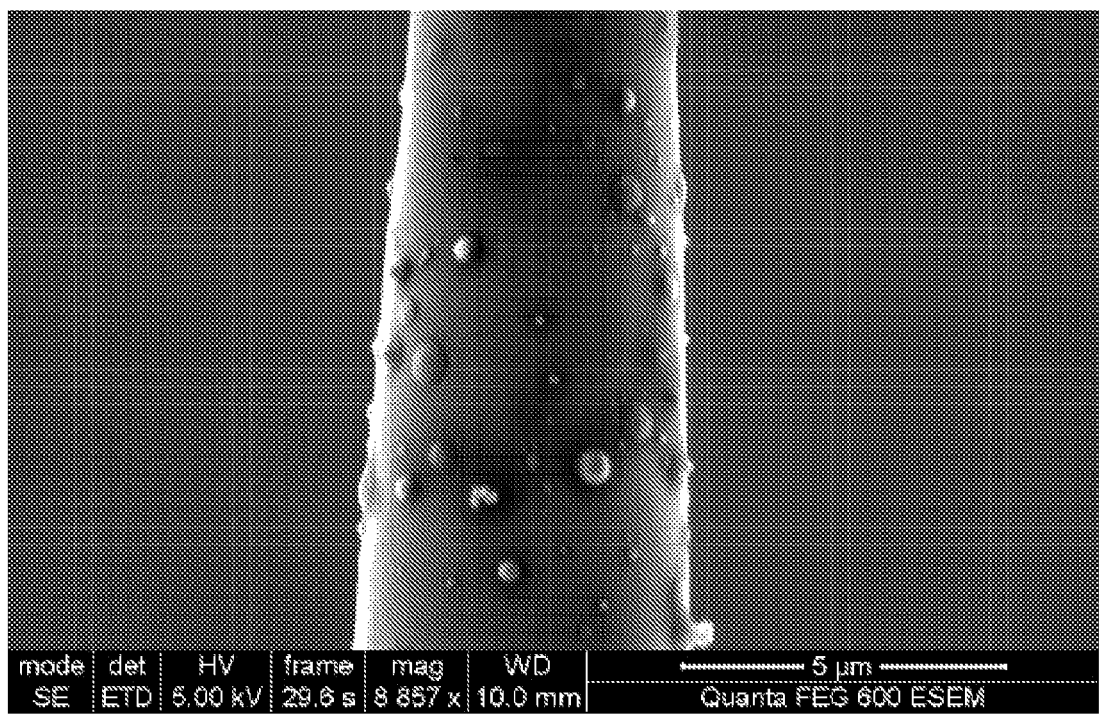
FIG. 18 illustrates a SEM image of a CNP coated with Ti (100 nm thickness)

When the titanium sputtered layer was comparatively thin (40 nm), the layer appeared to be smooth and continuous. FIG. 17 is an image of a titanium layer with a thickness of 40 nm sputtered on the outer surface of a pulled glass capillary. When the thickness of the sputtered layer was increased to 100 nm, some imperfections in the coating's uniformity were observed. FIG. 18 is an image of a titanium layer with thickness of 100 nm sputtered on a pulled quartz capillary. The Ti layer is continuous, but not as smooth as the 40 nm Ti layer shown in FIG. 1. Witness the presence of "pimple-like" features in FIG. 2.

The Effect of the Oil Layer on BHF Etching

Figure 19:
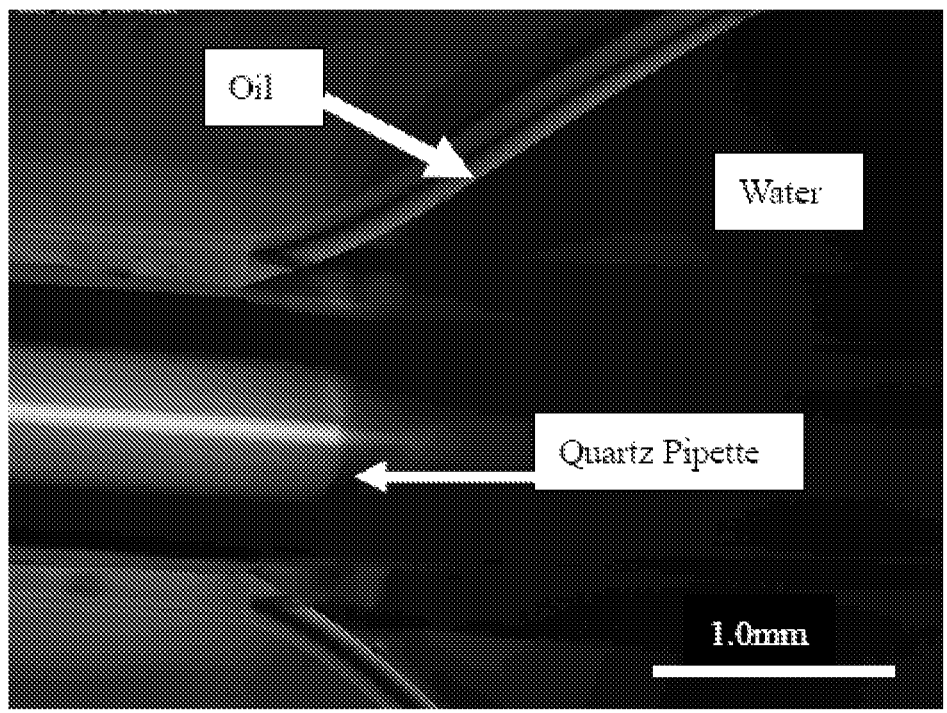
FIG. 19 illustrates an optical microscope image of the quartz pipette submerged in water covered with a thin film of oil.

FIG. 19 is an optical microscope image of a quartz pipette submerged in water with an oil film on the water's surface. Due to contact angle effects, the water climbs along the outer surface of the pipette. When the edge of the pipette is level with the water/oil-air interface (far from the capillary), the capillary rise is approximately 500 μm. Thus, when monitoring the electric current upon contacting the CNP with the BHF solution, it is anticipated that about 500 μm of the titanium's length are in contact with the BHF solution and will be etched away. When one desires to reduce the etched length, one will need to retract (raise) the CNP quickly by a predetermined amount—when contact with the BHF solution has been detected. The etching process lasts about 100 seconds. It is anticipated, however, that, in most cases, the etching length of ~200 μm is acceptable. In the absence of the oil film, a much longer segment of the titanium coating was etched.

Figure 20:
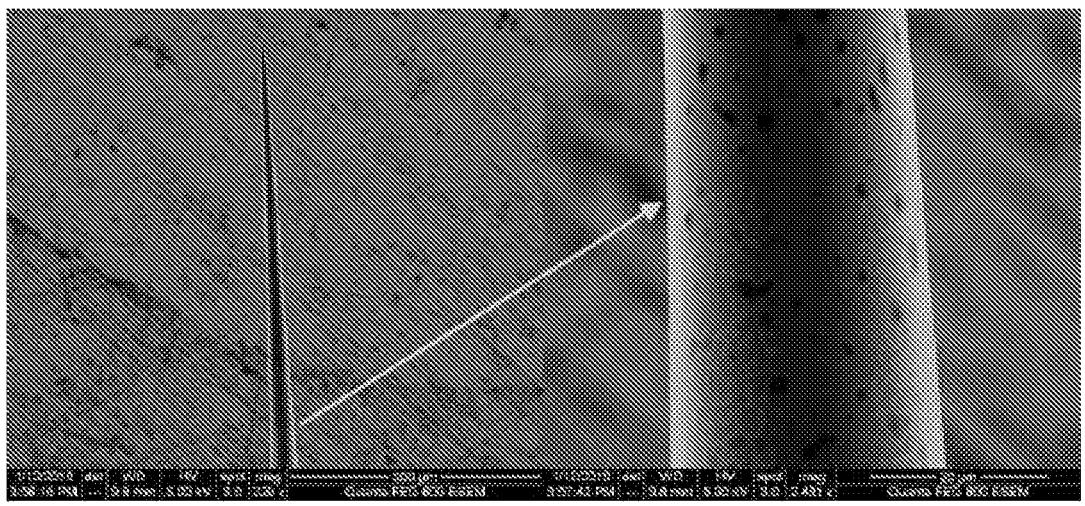
FIG. 20 illustrates SEM images of an etched CNP initially coated with 40 nm of Ti. The etching was carried out in BHF solution covered with a thin film of oil.

FIG. 20 shows images of the BHF effect on 40 nm thick Ti sputtered layer when etching was carried out with a BHF solution covered with a film of oil. The CNP was lowered into a BHF solution (covered with an oil film). The dipping (lowering of the CNP) was stopped as soon as an electric current was detected. The pipette was dipped in the BHF solution for 75 s. As a result, a length of about 510 μm (measured from the CNP's tip) of titanium was etched. The interface between the bare glass and the unetched titanium is not readily visible in FIG. 4 perhaps due to the thiness of the titanium coating.

Figure 23:
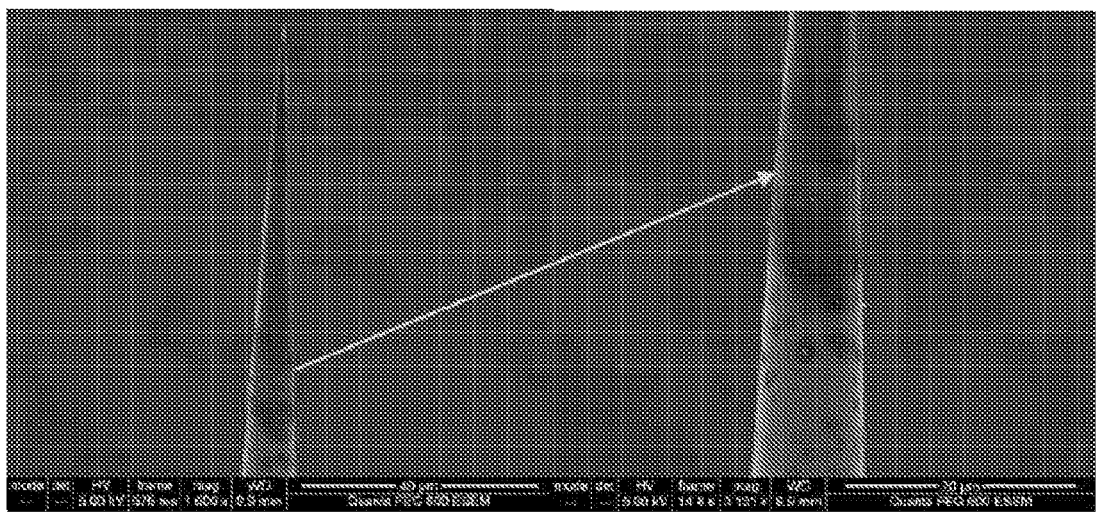
FIG. 23 illustrates SEM images of a CNP sputtered with 100 nm titanium and etched in oil-covered BHF.

The interface between the etched portion of the glass and the unetched titanium is more clearly visible when the titanium layer is thicker such as in the case of FIG. 23, which shows a CNP coated with 100 nm of titanium. The pippette was exposed to the BHF solution for 120 s resulting in about 72 μm of the titanium length being etched. The interface between the etched and unetched parts of the CNP is clearly visible as indicated by the arrow in FIG. 23.

Figure 21:
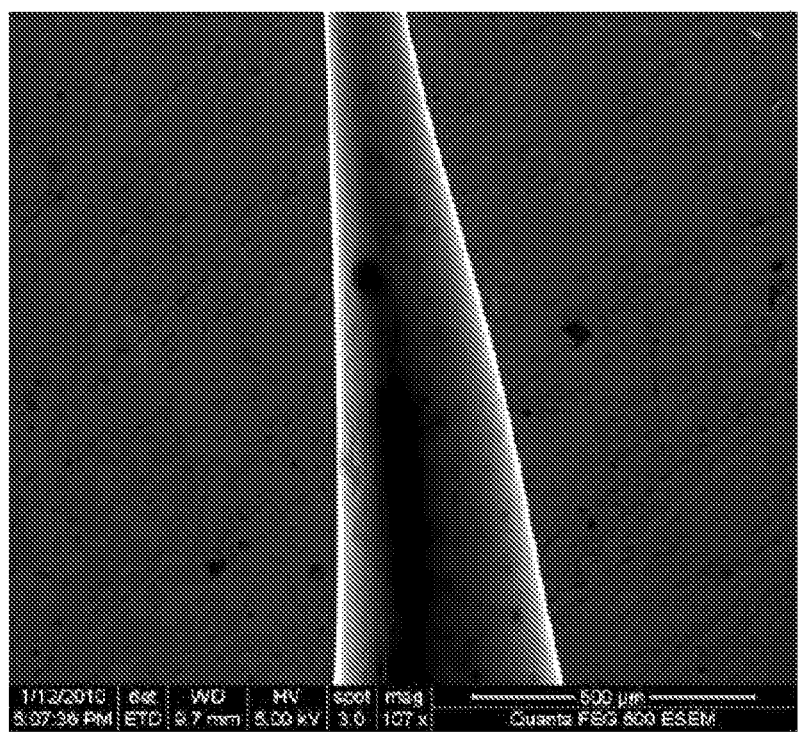
FIG. 21 illustrates SEM image of etched CNP sputtered with 40 nm of Ti. The CNP was dipped in BHF covered with oil.

When the BHF solution was not covered with an oil film, the interface between the etched portion of the glass and the titanium coating was not apparent (FIG. 21). Without being bound to any particular theory, this is perhaps due to the high capillary rise of the BHF solution, which caused etching of a substantial length of the titanium film (with the interface position being outside the field of view of the STEM) and due to possible additional etching by BHF vapor.

Figure 22:
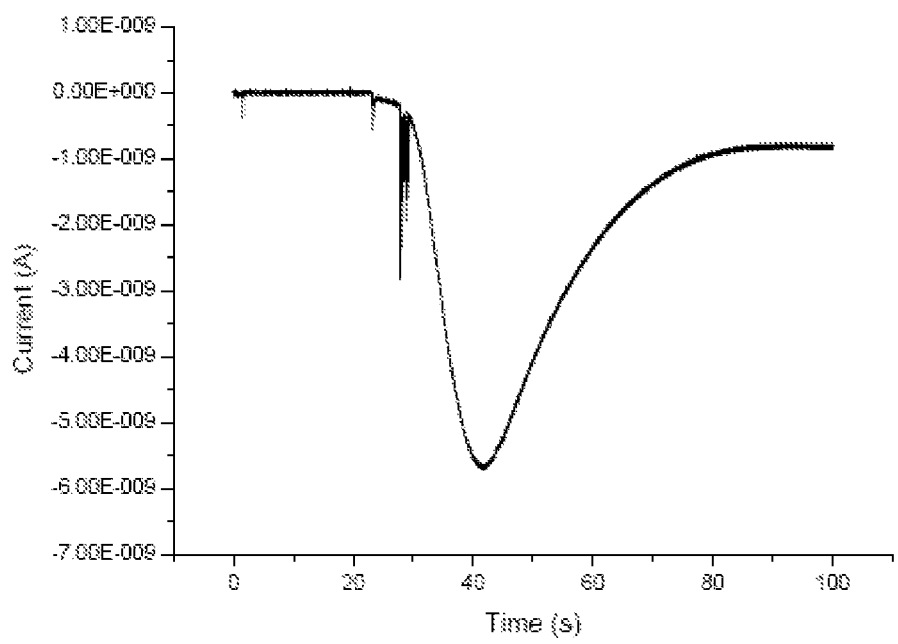
FIG. 22 illustrates the electric current as a function of time. The CNP, coated with 40 nm titanium, was lowered into oil—coated BHF solution. The dipping process was stopped as soon as electric current was recorded.

FIG. 22 depicts a typical relationship between the current and the submersion time of a CNP coated with 40 nm of titanium. The titanium-coated CNP is lowered into the BHF solution until an electric current is detected. As soon as a current had been detected, the descent of the CNP was halted. Nevertheless, the current magnitude initially increased. The time constant associated with the current rise appears much longer than the time constant associated with the capillary ascent. Without being bound to any particular theory, it is anticipated that the capillary rise of the BHF solution upon contact is a very rapid process, potentially on the scale of ms. The increase in the current may be due to the dissolution of a $TiO_2$ insulating layer that formed along the outer surface of the Ti coating. Once the $TiO_2$ layer disappeared, the current's magnitude peaks.

As the titanium layer is being etched, the effective surface area of the electrode decreases and the current decreases. This hypothesis may be supported by estimating the number of atoms in the titanium layer and comparing it with the amount of electric charge (the integral of the current with respect to time) transmitted through the electrode. The current does not decay back to zero as time goes by, and instead reaches an asymptotic value of about −1 nA. Without being bound to any single theory, one possibility for the current's failure to return to zero is that the external titanium coating makes contact with the carbon film at the un-pulled end of the capillary and the current is conducted through the carbon film.

The Effect of the Metal Layer's Thickness

FIG. 23 is a SEM image of an etched CNP initially sputtered with a 100 nm thick layer of titanium. The interface between the etched and unetched parts of the surface is clearly visible. About 72 μm length (measured from the tip) of the Ti layer was etched.

Figure 24:
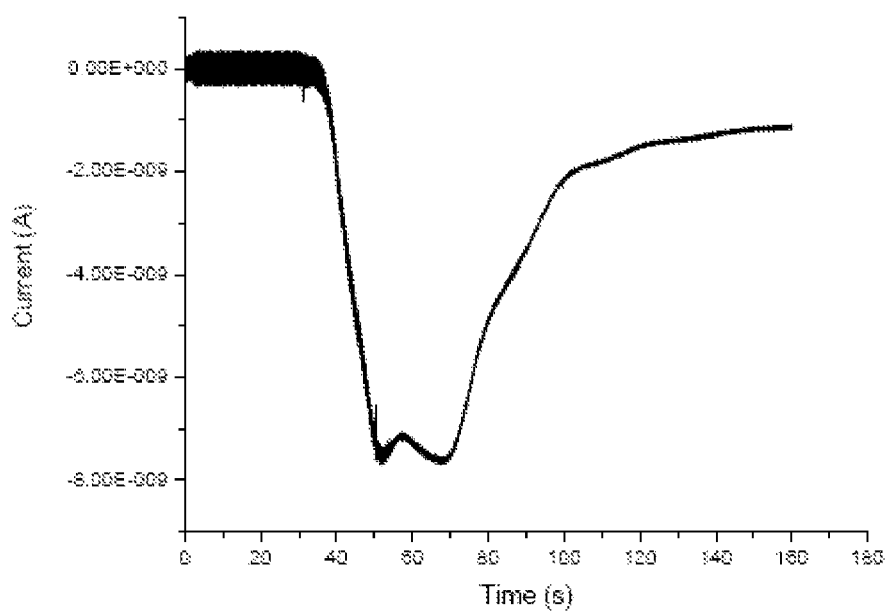
FIG. 24 illustrates electric current as a function of time. The CNP, coated with 100 nm titanium, was lowered into oil—coated BHF solution. The dipping process was stopped as soon as electric current was recorded. Witness the presence of two current peaks.

FIG. 24 depicts the measured current as a function of time when a CNP coated with 100 nm of titanium was submerged in the BHF solution. The CNP was lowered slowly into a BHF solution covered with a thin film of mineral oil. As soon as an electric current was registered, the CNP's descent was halted. Once electric contact was established, the current's magnitude increased with time, attained a peak, declined slightly, increased again, attained a second peak, and then declined to a lower asymptotic level (albeit not to zero) of about −1 nm. FIG. 24 should be compared with FIG. 22.

In the case of the thicker titanium layer, the current peak lasted longer—about twice as long as in FIG. 22, which is consistent with the titanium layer being twice as thick. The initial increase in the current is attributed to the dissolution of the titanium oxide insulating layer as in FIG. 22. The second peak may result from uneven etching, which may cause a temporary increase in the surface area of the titanium layer in contact with the BHF solution. The double peak appeared in some (FIGS. 24 and 28), but not all (FIG. 29) cases. The fact that the current eventually attains an asymptotic magnitude of approximately −1 nA supports the theory that this current is transmitted through the carbon film.

Reproducibility

FIGS. 20-33 depict SEM images of etched titanium-coated pipettes and the corresponding current-voltage relationship. Some of the data is summarized in the tables below. Tables 1 and 2 provide, respectively, document the length of the exposed titanium layer for pipettes coated with a 40 nm thick layer and 100 nm tick layer.

TABLE 1

CNPs coated with 40 nm titanium layer

| # | Length of exposed (etched) quartz (μm) | SEM image | Current-time | Comments |
|---|---|---|---|---|
| 1 | 510 | FIG. 20 | FIG. 22 | |
| 2 | 150 | FIG. 26 (a) | FIG. 26 (b) | |

TABLE 2

CNPs coated with 100 nm titanium layer

| # | Length of exposed (etched) quartz (μm) | SEM image | Current-time | Comments |
|---|---|---|---|---|
| 1 | 72 | FIG. 27 (a) | FIG. 27 (b) | |
| 2 | 43 | FIG. 28 (a) | FIG. 28 (b) | |
| 3 | 55 | FIG. 29 (a) | FIG. 29 (b) | |

The etched length of the 40 nm thick titanium varied considerable from one experiment to another and ranged from 150 μm to 510 μm. The scatter of the etched length in the case of the thicker titanium layer (100 nm) was significantly smaller and ranged from 42 to 90 μm. The large variations of the thin (ca. 40 nm) titanium layer's etched length may be due sputtering process non uniformities. Depending on the application, the recorded variation may be of little to no significance.

Figure 34:
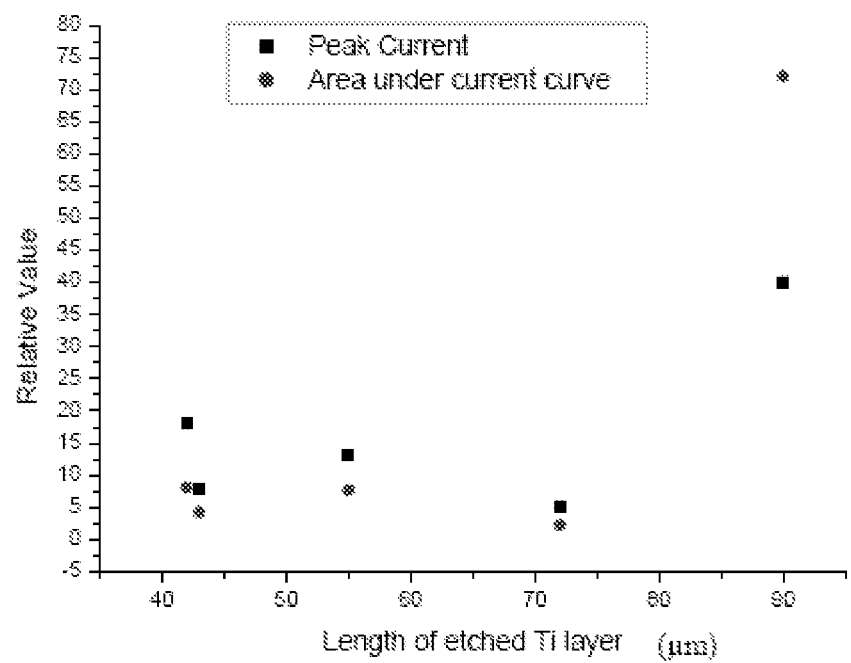
FIG. 34 illustrates the current peak's magnitude and the current peak's area as functions of Ti etched length. The thickness of the titanium layer is 100 nm.
Figure 35:
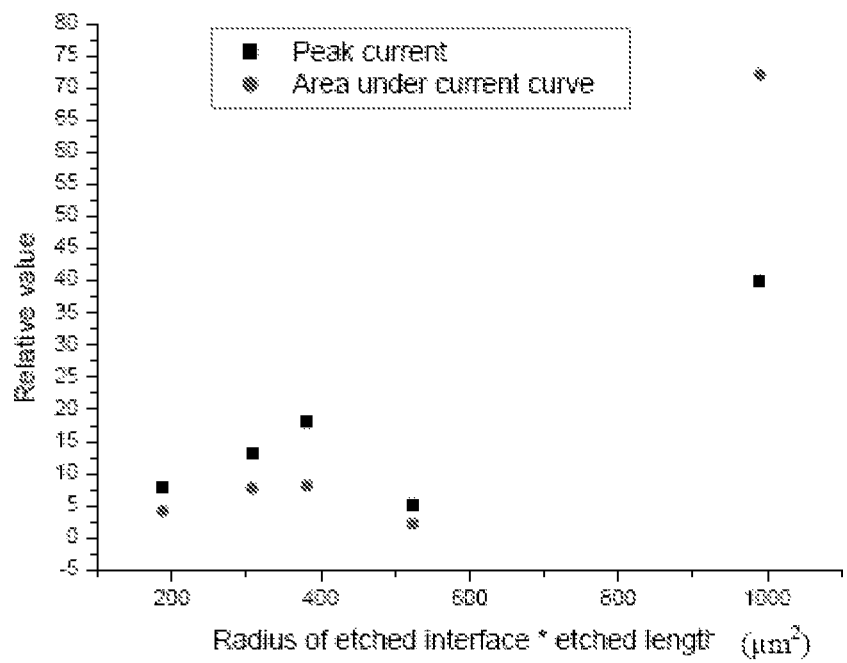
FIG. 35 illustrates the current peak's magnitude and the current peak's area as functions of the (radius of etched interface)*(Ti etched length). The thickness of the titanium coating is 100 nm.

A related question is whether the length of the etched titanium layer can be estimated from the current-time relationship. FIG. 34 depicts the magnitude of the current peak and the area of the peak in arbitrary units as functions of the etched length when the titanium coating thickness is 100 nm. Although the current peak magnitude and the area under the peak increase as the etched length increases, the relationship is not monotonic. This may be due to variations in the radii of the pipettes' tips. FIG. 35 depicts the magnitude of the current peak and the area under the peak (in arbitrary units) as functions of the product of etched length and the radius of the pipette. As shown, the peak's magnitude and the area under the peak increase nearly linearly with the product of the etched length and the pipette tip's radius (at the interface between the etched and un-etched parts).

In sum, disclosed is successful deposition of a metal layer on the outer surface of the CNP and the etching of a length of the metal coating. While titanium was used here, depending on the intended use of the metal coated CNP, other metals can be used such as silver.

Also disclosed is a process to facilitate the etching of the metal from the CNP's tip. The process is based on using the metal coating to detect the instant when the CNP makes contact with the etching solution. By monitoring the electric current during the etching process, we can obtain information on the process. The electric current's peak magnitude and the area under the peak provide information about the length of metal that is being etched.

Additional Embodiments

Metal-Enhanced Tips

Also provided are probes having metal coated tips and also related methods of fabricating such pipettes. As demonstrated herein, the metal coating enhances the functionality of the carbon nanopipettes and reduces the signal noise that may be inherent in the devices.

A metal (e.g., silver) coating enables the user to form silver chloride electrode, which allows one to carry out low noise, high precision electrical measurements with living cells. Gold coating enables one to take advantage of the highly-developed gold chemistry to attach biological molecules to the gold-coated carbon tip. These metal coated electrodes have many applications in cell studies.

Figure 36:
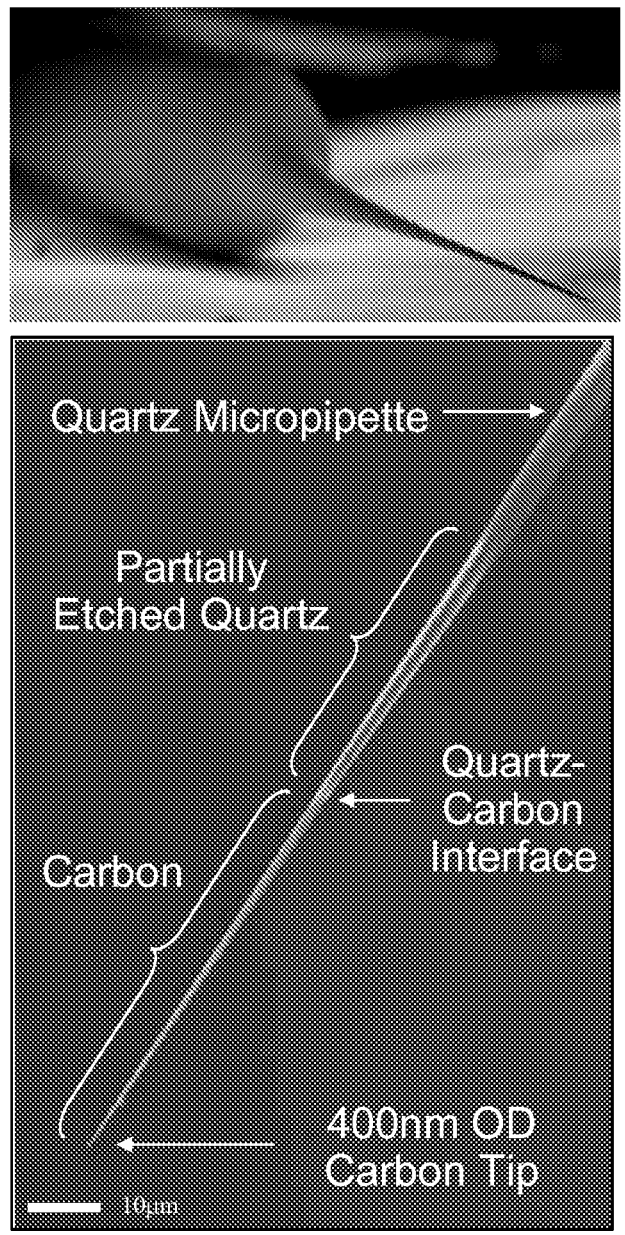
FIG. 36 illustrates scanning electron micrographs of CNPs.

As described in U.S. patent application Ser. No. 11/231, 425 (incorporated herein by reference), carbon-based nanopipettes (CNP) have been developed that do not require any assembly (FIG. 36). Such CNPs suitably include of a pulled glass capillary terminating with an exposed carbon pipe with a diameter ranging from tens to hundreds of nanometers. The inner lumen of the glass capillary is coated with a carbon film that provides an electrically conducting path from the distal end of the capillary to the exposed carbon tip.

CNPs can be used in a variety of applications ranging from nozzles for nano-printing to cellular probes to bio/chemical sensors. Most of our work to date focused on the use of CNPs as cellular probes. Among other things, the CNPs can be used to evaluate new drugs and answer fundamental questions in biology and medicine.

The CNPs can penetrate a cell's membrane without causing damage to the cell, can be used to inject controllably reagents into cells, and measure cell's electrical potential. The CNPs offer significant advantages over the commonly used pulled glass pipettes such as smaller size (minimally damaging to cells and the ability to probe organelles), better mechanical properties, higher durability (they do not break or clog easily), potential for automation (the cell's penetration can be sensed through an electric signal conducted through the carbon lining), ability to carry out electrophysiological measurements concurrently with injection, and multifunctional analytic capabilities while being competitive in price with the commonly used glass micropipettes.

Furthermore, given their durability, the CNPs offer higher efficiency and lower cost (on a per cell basis) than their glass counterparts. The CNPs also allow predictable and controllable introduction of reagents into cells. In contrast, alternative techniques of introducing reagents into cells through electro/photo/chemo poration lack control of the quantity and composition of the material penetrating the cell. The CNPs are also compatible with commonly used laboratory equipment such as femtoinjectors and micromanipulators.

Here are described methods to selectively coat the CNP's carbon tip with metals such as (but not limited to) silver and gold to form metal electrodes. While the carbon nanopipette provides a relatively low resistance conductive path, the small surface area of the exposed carbon that is in contact with the electrolyte solution exhibits a relatively high junction impedance.

While the carbon tip can be used to measure cell membrane potential (Schrlau et al., 2009a), this measurements are challenging and require high impedance instrumentation. To reduce the junction resistance, the user suitably electroplates the carbon tip with silver. The electroplating process enables one to selectively coat the carbon tip without coating the glass or quartz.

Obtaining good metal coverage is, however, not trivial. First, the metal may crystallize and form discrete islands on the carbon surface. To overcome this difficulty, the present invention provides a multi-step electrochemical coating technique to obtain relatively uniform metal (e.g., silver) coating. A silver layer can be chlorinated to form a remarkably low noise silver-chloride electrode. Related techniques can be used to coat the carbon tip with gold, which enables the user to take advantage of the highly developed gold chemistry to attach various macromolecules to the carbon tip surface, position the tip at predetermined locations inside the cell, and carry out cell studies with high spatial resolution.

Methods

A quartz tube (OD: 1.0 mm; ID: 0.7 mm) was pulled to form a pipette with a sharp tip (ID: ~260 nm). Smaller diameter tips are also possible. The tube was inserted into a furnace and exposed to flow of hydrocarbon precursor gas mixed with argon at ~900° C.

After 3 hours of chemical vapor deposition (CVD), a continuous ~60 nm thick carbon lining film formed along the entire inner surface of the quartz pipette from tip to distal end. Hence, the product of the CVD process consists of an outer insulating quartz layer and an inner, electrically conductive, mostly amorphous carbon layer. The carbon tip (OD: ~260 nm) was exposed by etching away the outer quartz layer to a desired extent. The resulting nano carbon tip can be used as a nanoelectrode. In these non-limiting embodiments, the CNPs were etched for 2 minutes to expose ~10 μm of carbon pipe.

To limit metal deposition to the carbon tip and avoid damaging the tip, electroplating is preferred to vapor deposition methods because it facilitates selective coating only on conductive surfaces. The electroplating method may result in nonuniform metal deposition wherein metal nucleates on the carbon surface and forms isolated, disconnected crystals that grow both perpendicular to and along the carbon surface.

Provided here are methods for electrochemically coating the carbon tip with a metal Silver is described here for exemplary purposes only; the claimed methods should be be interpreted as being limited to silver.

The electrochemical deposition of silver on the tip of CNP was performed in the silver Cy-less II commercial solution (Technic Inc). The silver solution was modified by adding isochoric 2.0 mM silver nitrate (Fisher >99.95%) to increase the silver ion concentration and the deposition current. Electrodeposition was controlled with a HEKA patch clamp amplifier EPC 10 (two electrode mode). A silver wire provided a reference/counter electrode. The wire was immersed directly in the plating solution. Silver deposition was affected by stepping double-pulse potential on the CNP tip. The quality of the electroplating silver layer was examined with SEM. The chloride transformation of the silver coating to a silver chloride electrode was performed in 0.5M KCl solution.

Results and Discussion

Figure 37:
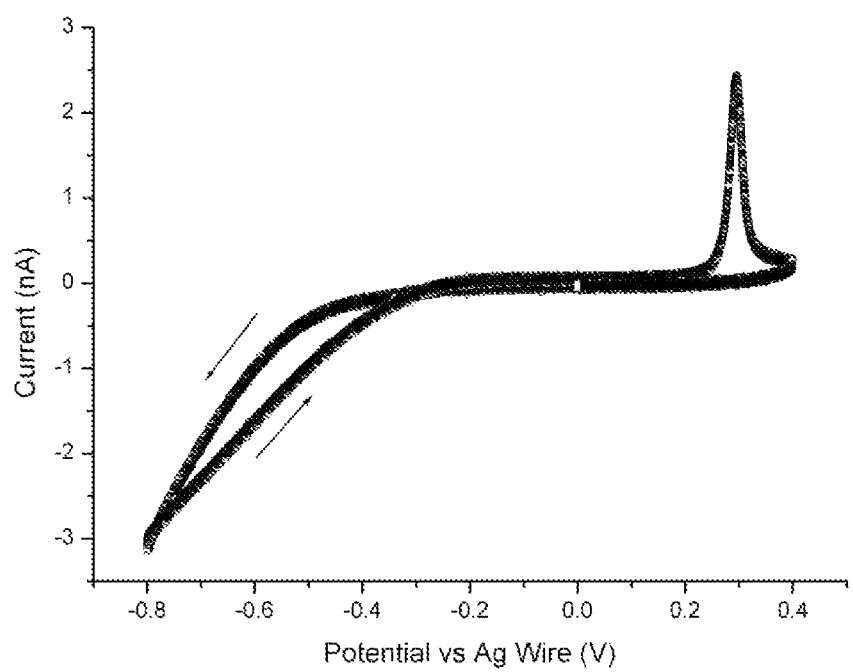
FIG. 37 illustrates the current-potential profile of silver coating of carbon tip recorded at 100 mV/s in modified Silver Cy-less II commercial solution.

The cyclovoltammograms corresponding to the silver electrodeposition and electrodissolution on the carbon tip were recoded at 100 mV/s by setting the anodic switching potential as low as possible to avoid the electrooxidation of the carbon tip. The voltammogram (FIG. 37) shows that the silver starts to deposit at −200 mV and dissolves at +240 mV vs Ag wire reference electrode. The reverse scan exhibits a hysteresis loop involving a cathodic current greater than that recorded in the preceding negative potential ascending scan. Without being bound to any particular theory, it is proposed that the loop is related to the nucleation and 3D growth of silver crystals.

Potentiostatic deposition of silver on the CNP tip was accomplished by double-pulsing the potential of the exposed carbon tip. The working parameters were to pulse the potential from 0 mV to −900 mV for 400 ms, followed by reducing the potential to −600 mV for 100 s.

Figure 38:
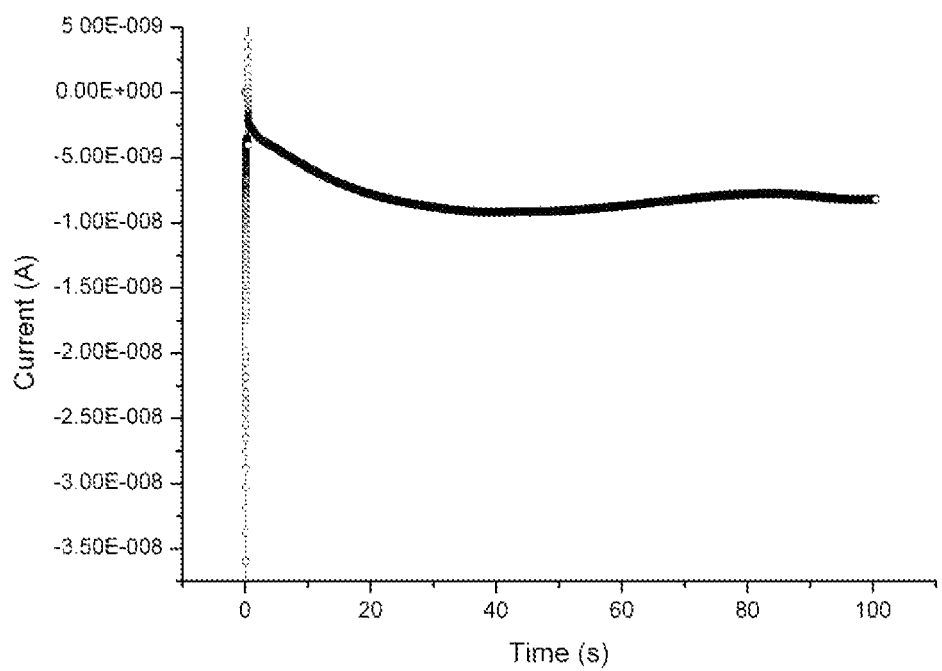
FIG. 38 illustrates electrical current as a function of time during the double pulses deposition.
Figure 39:
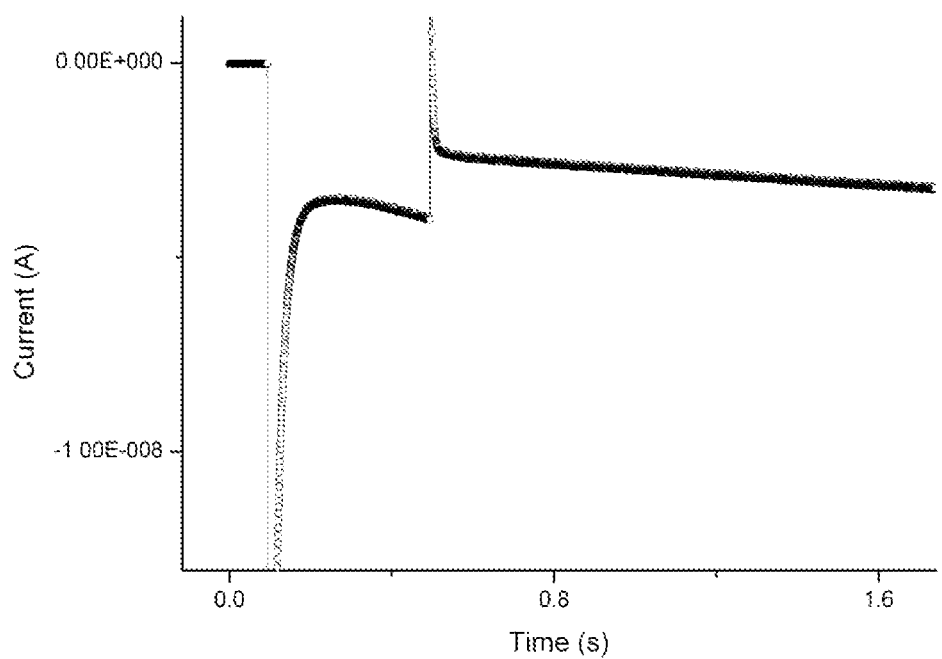
FIG. 39 illustrates electric current as a function of time during the first potential pulse. The figure is an enlargement of an early time portion of FIG. 38.
Figure 40:
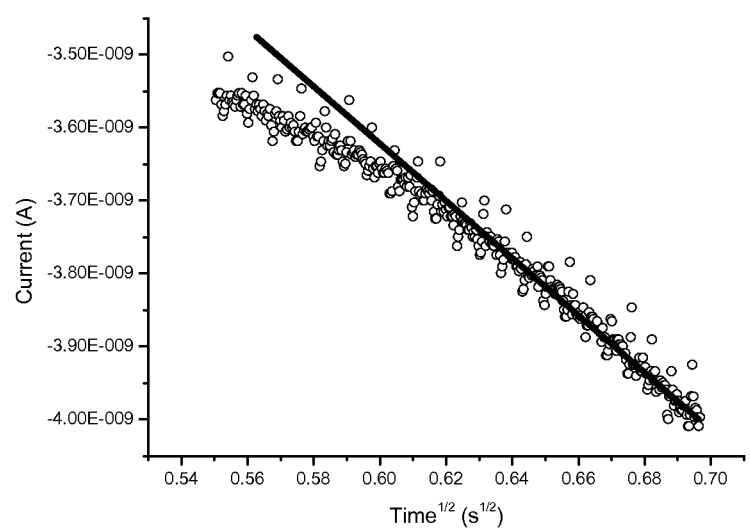
FIG. 40 illustrates the $I(t) \propto t^{1/2}$ dependence following the first potential pulse.

Representative current-time transients are depicted in FIGS. 38 and 39. FIG. 39 is an enlargement of the early time transient of FIG. 38. During the first pulse (FIG. 39), one observes a typical double layer charging current followed by a typical three dimensional growth current with (FIG. 40). The current data associated with the first pulse likely indicates instantaneous nucleation and three-dimensional deposition growth mode. The slow increase in the absolute value of the current (FIGS. 38 and 39) may be due to the increase in the surface area of the silver layer. Once silver islands start to merge, the silver area may decrease, which may explain the wave form observed in FIG. 38.

FIG. 41 shows a SEM image of the silver coated tip, illustrating a relatively smooth, thin silver layer. When the electroplating is carried out with a standard solution and with a single potential step, the resulting coating consists of disconnected silver islands (crystals), as shown in FIG. 42.

Figure 8:
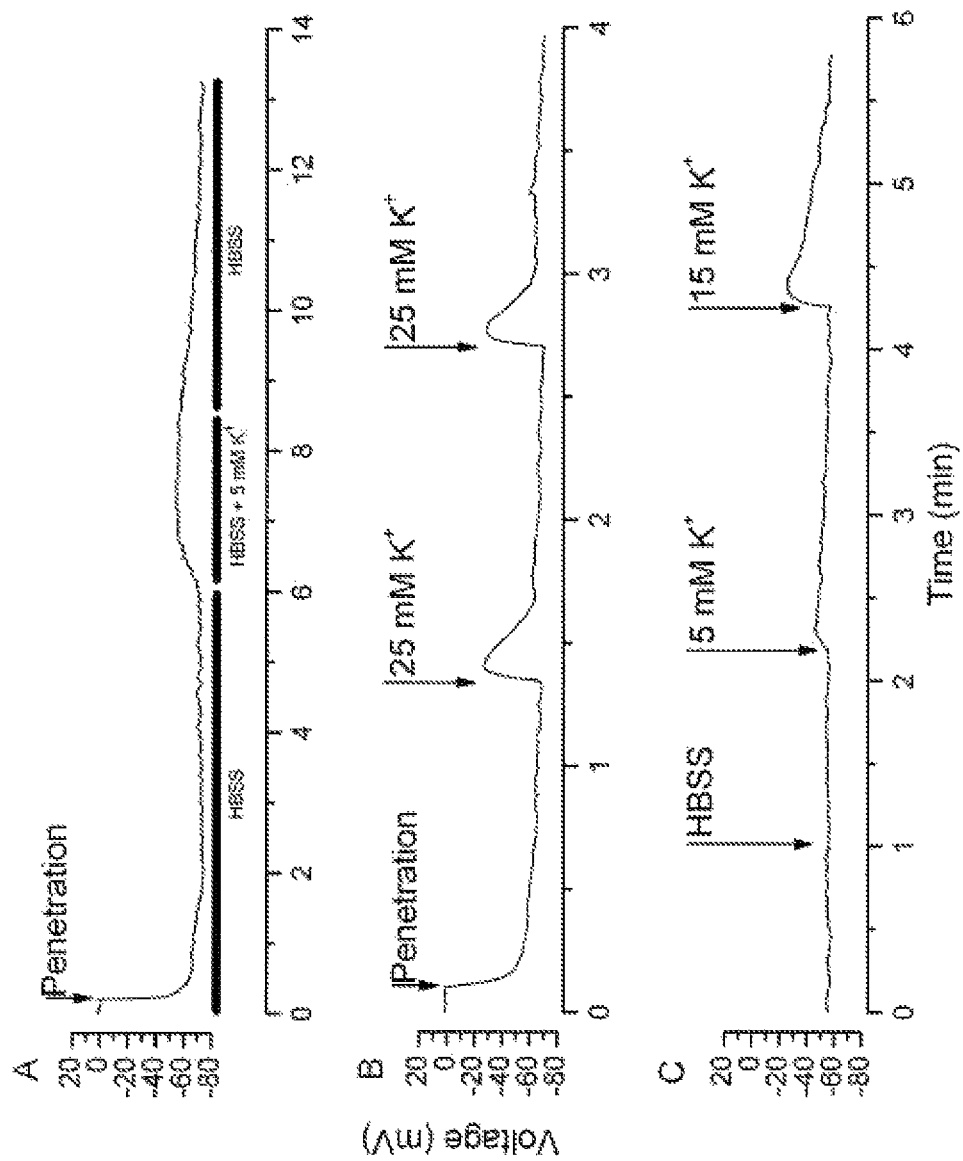
FIG. 8 illustrates CNP-recorded variations in membrane potential during ionic enrichment. (A) Variations as a function of time during a short perfision interval (~2 min, middle horizontal bar) with K+-enriched HBSS (additional 5 mM $K^+$). (B) Variations as a function of time during the repetitive K+-enrichment of HBSS (additional 25 mM $K^+$). (C) Variations as a function of time during the administration of normal HBSS and the varied K+-enrichment of HBSS (additional 5 and 15 mM $K^+$)
Figure 43:
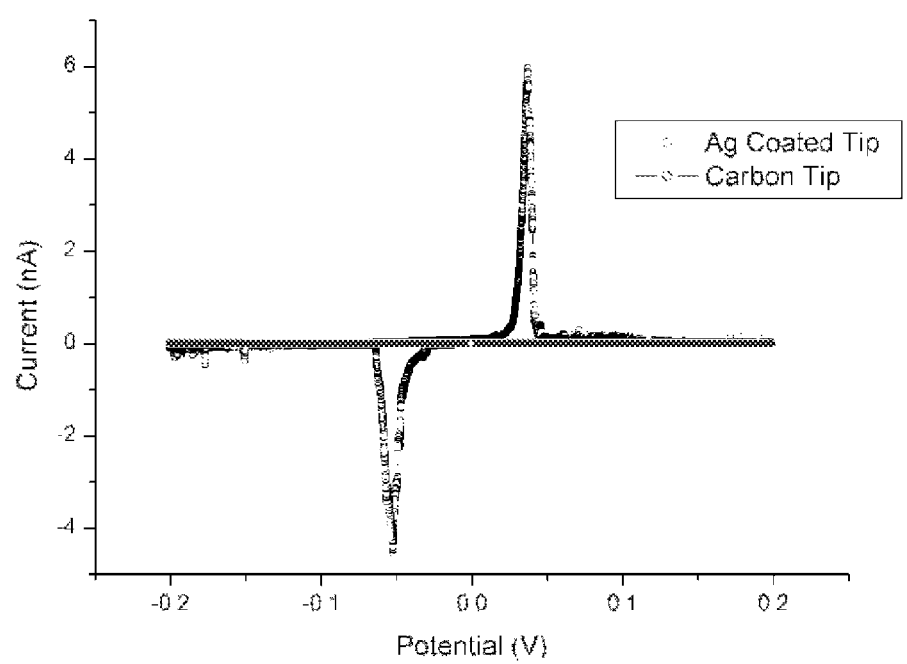
FIG. 43 illustrates cyclic voltammetry of carbon tip and AgCl/Ag/Carbon tip in 0.5M KCl with scan rate of 20 mV/s.

The outer surface of the silver layer was transformed to AgCl by applying 30 mV (vs Ag wire) in 0.5M KCl for 20 seconds. Unpolarization of AgCl/Ag/Carbon tip and the polarization of carbon tip were characterized by cyclic voltammetry (20 mV/s) in 0.5M KCl, as shown in FIG. 8. The AgCl/Ag/Carbon tip was very close to the ideal unpolarizable electrode. The carbon tip was very close to the ideal polarizable electrode. As shown in FIG. 43, the signal was very low noise.

The disclosed metal coatings are suitably applied to the CNP tips described in U.S. patent application Ser. No. 11/231,425 and to the tips of the multi-electrode probes described in the instant application. The coatings may thus be used to improve the electronic performance of these devices as well as of other probe devices, as the disclosed technology may be applied to a variety of shapes, forms, and devices.

Summary

Traditionally, electrolyte-filled, glass-based electrodes have been used to monitor cell membrane potentials. The preceding demonstrates the utility of carbon nanopipettes (CNPs) as ohmic nanoelectrodes for intracellular electrophysiological recording. CNPs recorded the electrical responses of cells to pharmacological agents, the values of which matched well with predictions from the Nernst equation. Using CNPs, it was demonstrated that HT-22 cells hyperpolarize via the GABAA receptor in response to extracellular administration of GABA.

CNPs and other electrodes according to the claimed invention have a number of advantages over glass-based electrodes. First, they facilitate lengthy measurements without ions diffusing from the hollow of the electrode into the cell and they are less likely to break and clog during use. Second, CNPs have the capability of facilitating concurrent intracellular injection and electric measurements, making them well-suited for multifunctional cell probing. Third, it was demonstrated that cell penetration can be sensed electrically, which can facilitate the automation of cell injection.

What is claimed:

1. A probe, comprising:
    an elongate insulator having a distal terminus and a lumen, the lumen having a diameter of from about 1 nm to about 1 cm;
    a first conductive layer on the inner surface of the lumen and in electrical communication with a first contact, wherein the first conductive layer comprises carbon and wherein at least a portion of the first conductive layer extends beyond the distal terminus of the elongate insulator, said portion of the first conductive layer that extends beyond the distal terminus of the elongate insulator being at least partially surmounted by a metal; and
    a second conductive layer surmounting at least a portion of the outer surface of the elongate insulator and in electrical contact with a second contact, wherein the second conductive layer terminates at a position remote from the distal terminus of the elongate insulator.

2. The probe of claim 1, wherein the elongate insulator is characterized as circular in cross-section.

3. The probe of claim 1, wherein the elongate insulator is characterized as polygonal in cross-section.

4. The probe of claim 1, wherein the elongate insulator has a variable cross-section.

5. The probe of claim 1, wherein the elongate insulator comprises a dielectric material.

6. The probe of claim 1, wherein the dielectric material comprises silica, silica nitride, glass, quartz, polymer, plastic, or any combination thereof.

7. The probe of claim 1, wherein the lumen of the elongate insulator has a diameter in the range of from about 10 nm to about 10000 nm.

8. The probe of claim 1, wherein the lumen of the elongate insulator has a diameter in the range of from about 100 nm to about 1000 nm.

9. The probe of claim 1, wherein the elongate insulator has a wall thickness in the range of from about 1 nm to about 10 micrometers.

10. The probe of claim 1, wherein the second conductive layer comprises carbon, metal, a conductive polymer, or any combination thereof.

11. The probe of claim 10, wherein the metal comprises gold, silver, chromium, titanium, tungsten, platinum, aluminum, nickel, or any combination thereof.

12. The probe of claim 1, wherein the first conductive layer has a thickness in the range of from about 1 nm to about 10 micrometers.

13. The probe of claim 1, wherein the first conductive layer defines a lumen.

14. The probe of claim 1, wherein the first conductive layer fills the entirety of the lumen of the elongate insulator.

15. The probe of claim 1, wherein the second conductive layer has a thickness in the range of from about 1 nm to about 10 µm.

16. The probe of claim 1, further comprising a second elongate insulator disposed adjacent to the second electronically conductive layer.

17. The probe of claim 16, further comprising a third conductive layer surmounting at least at portion of the second elongate insulator, the third conductive layer being in electrical communication with a third contact.

18. The probe of claim 16, wherein the second elongate insulator is coaxial with the first hollow elongate insulator.

19. The probe of claim 17, further comprising a third elongate insulator disposed adjacent to the third conductive layer.

20. The probe of claim 19, further comprising a fourth conductive layer, the fourth conductive layer surmounting at least a portion of the third elongate insulator, and the fourth conductive layer in electrical communication with a fourth contact.

21. The electronic probe of claim 1, further comprising an injector in fluid communication with the lumen.

22. The electronic probe of claim 1, wherein the metal comprises silver, gold, platinum, or any combination thereof.

23. The electronic probe of claim 1, wherein the metal comprises a thickness in the range of from about 5 nm to about 1 micron.

24. The electronic probe of claim 23, wherein the metal comprises a thickness in the range of from about 10 nm to about 500 nm.

25. The electronic probe of claim 24, wherein the metal comprises a thickness in the range of from about 50 nm to about 100 nm.

26. The probe of claim 1, wherein the first conductive layer further comprises a conductive polymer.

* * * * *